(12) United States Patent
Arakawa et al.

(10) Patent No.: US 7,541,371 B2
(45) Date of Patent: Jun. 2, 2009

(54) METHOD FOR TREATING A MOTOR NEURON DISEASE

(75) Inventors: Yoshihiro Arakawa, Ibaraki-ken (JP); Makoto Miyazaki, Kanagawa-ken (JP)

(73) Assignee: Eisai R&D Management Co., Ltd., Tokyo-To (JP)

( * ) Notice: Subject to any disclaimer, the term of this patent is extended or adjusted under 35 U.S.C. 154(b) by 18 days.

(21) Appl. No.: 11/707,883

(22) Filed: Feb. 20, 2007

(65) Prior Publication Data

US 2008/0027039 A1    Jan. 31, 2008

Related U.S. Application Data

(60) Provisional application No. 60/774,544, filed on Feb. 21, 2006, provisional application No. 60/874,247, filed on Dec. 12, 2006.

(51) Int. Cl.
*A61K 31/445* (2006.01)
(52) U.S. Cl. ...................................... 514/323
(58) Field of Classification Search ................. 514/323
See application file for complete search history.

(56) References Cited

U.S. PATENT DOCUMENTS

| 6,340,759 B1 | 1/2002 | Ueno et al. |
| 2005/0256103 A1 | 11/2005 | Suzuki et al. |
| 2007/0219179 A1 | 9/2007 | Suzuki et al. |

FOREIGN PATENT DOCUMENTS

| JP | 2005-225845 | 8/2005 |
| WO | 98/43956 | 10/1998 |
| WO | 99/18077 | 4/1999 |
| WO | 02/078643 | 10/2002 |
| WO | 2005/108389 | 11/2005 |

OTHER PUBLICATIONS

CLG Lin, et al., "Abberant RNA processing in a neurodegenerative disease: the cause for absent EAAT2, a glutamate transporter, in amyotrophic lateral sclerosis", *Neuron*, vol. 20, pp. 589-602, Mar. 1998.
T Meyer, et al., "The RNA of the glutamate transporter EAAT2 is variably spliced in amyotrophic lateral sclerosis and normal individuals", *J. Neur. Sci.*, vol. 170, pp. 45-50, 1999.
HX Deng, et al., "Amyotrophic lateral sclerosis and structural defects in Cu,Zn superoxide dismutase", *Science*, vol. 261, pp. 1047-1051, Aug. 1993.
DR Rosen, et al., "Mutations in Cu/Zn superoxide dismutase gene are associated with familial amyotrophic lateral sclerosis", *Nature*, vol. 362, pp. 59-62, Mar. 4, 1993.
M Nagai, et al., "Rats expressing human cytosolic copper-zinc superoxide dismutase transgenes with amyotrophic lateral sclerosis: associated mutations develop motor neuron disease", *J. Neurosci.*, vol. 21, No. 23, pp. 9246-9254, Dec. 1, 2001.

ME Gurney, et al., "Motor neuron degeneration in mice that express a human Cu,Zn superoxide dismutase mutation", *Science*, vol. 264, pp. 1772-1775, Jun. 17, 1994.
LP Rowland, et al., "Amyotrophic lateral sclerosis", *N. Engl. J. Med.*, vol. 344, No. 22, pp. 1688-1700, May 31, 2001.
JP Julien, et al., "Amyotrophic lateral sclerosis: unfolding the toxicity of the misfolded", *Cell*, vol. 104, pp. 581-591, Feb. 23, 2001.
Y Kawahara, et al., "RNA editing and death of motor neurons", *Nature*, vol. 427, pp. 801, Feb. 26, 2004.
SA Lipton, et al., "Sporadic ALS: blame it on the editor", *Nature Medicine*, vol. 10, No. 4, pp. 347, Apr. 2004.
DW Cleveland and JD Rothstein, "From Charcot to Lou Gehrig: deciphering selective motor neuron death in ALS", *Nature Reviews: Neuroscience*, vol. 2, pp. 806-819, Nov. 2001.
HJL Fryer, et al., "Excitotoxic death of a subset of embryonic rat motor neurons in vitro", *J. Neurochem.*, vol. 72, No. 2, pp. 500-513, 1999.
G Bensimon, et al., "A controlled trial riluzole in amyotrophic lateral sclerosis", *New England Journal of Medicine*, vol. 330, No. 9, pp. 585-591, Mar. 3, 1994.
L Lacomblez, et al., "Dose-ranging study of riluzole in amyotrophic lateral sclerosis", *Lancet*, vol. 347, pp. 1425-1431, May 25, 1996.
Y Arakawa, et al., "Survival effect of ciliary neurotrophic factor (CNTF) on chick embryonic motoneurons in culture: comparison with other neurotrophic factors and cytokines", *J. Neurosci.*, vol. 10, No. 11, pp. 3507-3515, Nov. 1990.
DN Ishii and DJ Marsh, "On the therapeutic potential for insulin-like growth factor use in motor neuron disease", *Experimental Neurology*, vol. 124, pp. 96-99, 1993.
ME Lewis, et al., "Insulin-like growth factor-I: Potential for treatment of motor neuronal disorders", *Experimental Neurology*, vol. 124, pp. 73-88, 1993.
M Sendtner, et al., "Actions of CNTF and neurotrophins on degenerating motoneurons: preclinical studies and clinical implications", *Journal of the Neurological Sciences*, vol. 124 (Suppl.), pp. 77-83, 1994.
RM Lindsay, "Therapeutic potential of the neurotrophins and neurotrophin-CNTF combinations in peripheral neuropathies and motor neuron diseases", *Ciba Found Symp.*, vol. 196, pp. 39-53, 1996.
E Storkebaum, et al., "Treatment of motoneuron degeneration by intracerebroventricular delivery of VEGF in a rat model of ALS", *Nature Neuroscience*, vol. 8, No. 1, pp. 85-92, Jan. 2005.
H Thoenen and Michael Sendtner, "Neurotrophins: from enthusiastic expectations through sobering experiences to rational therapeutic approaches", *Nature Neuroscience supplement*, vol. 5, pp. 1046-1050, Nov. 2002.
Hans Hultborn and Ole Kiehn, "Neuromodulation of vertebrate motor neuron membrane properties", *Current Opinion in Neurobiology*, vol. 2, pp. 770-775, 1992.

(Continued)

*Primary Examiner*—Raymond J Henley, III
(74) *Attorney, Agent, or Firm*—Wenderoth, Lind & Ponack, L.L.P.

(57) ABSTRACT

According to the present invention, there is provided a method for treating a motor neuron disease, comprising the step of administering a therapeutically effective amount of a compound having serotonin receptor antagonist activity or its pharmacologically acceptable salt or their solvate optionally together with a pharmaceutically acceptable carrier to a mammal for which the treatment of said disease is indicated.

39 Claims, 5 Drawing Sheets

OTHER PUBLICATIONS

JF Perrier and J Hounsgaard, "5-HT$_2$ receptors promote plateau potentials in turtle spinal motoneurons by facilitating an L-type calcium current", *J. Neurophysiol.*, vol. 89, pp. 954-959, 2003.

DV Volgin, et al., "Postnatal development of serotonin 1B, 2A and 2C receptors in brainstem motoneurons", *European Journal of Neuroscience*, vol. 17, pp. 1179-1188, 2003.

JL Ridet, et al., "Direct immunocytochemical localization of 5-hydroxytryptamine receptors in the adult rat spinal cord: a light and electron microscopic study using an anti-idiotypic antiserum", *Journal of Neuroscience Research*, vol. 38, pp. 109-121, 1994.

T Hayashi, et al., "Developmental changes in serotonergic receptor-mediated modulation of embryonic chick motoneurons in vitro", *Developmental Brain Research*, vol. 102, pp. 21-33, 1997.

MY Wang and NJ Dun, "5-hydroxytryptamine responses in neonate rat motoneurones in vitro", *Journal of Physiology*, vol. 430, pp. 87-103, 1990.

EM Talley, et al., "Postnatal development of serotonergic innervation, 5-HT$_{1A}$ receptor expression, and 5-HT responses in rat motoneurons", *Journal of Neuroscience*, vol. 17, No. 11, pp. 4473-4485, Jun. 1, 1997.

M Antri, et al., "Locomotor recovery in the chronic spinal rat: effects of long-term treatment with a 5-HT$_2$ agonist", *European Journal of Neuroscience*, vol. 16, pp. 467-476, 2002.

O Bertel, et al., "Amyotrophic lateral sclerosis: changes of noradrenergic and serotonergic transmitter systems in the spinal cord", *Brain Research*, vol. 566, pp. 54-60, 1991.

BJ Turner, et al., "The serotonin precursor 5-hydroxytryptophan delays neuromuscular disease in murine familial amyotrophic lateral sclerosis", *ALS and other motor neuron disorders*, vol. 4, pp. 171-176, 2003.

Y Iwasaki, et al., "SR57746A: a survival factor for motor neurons in vivo", *Journal of the Neurological Sciences*, vol. 160 (Suppl. 1), S92-S96, 1998.

C Labie, et al., "Effect of the neuroprotective compound SR57746A on nerve growth factor synthesis in cultured astrocytes from neonatal rat cortex", *British Journal of Pharmacology*, vol. 127, pp. 139-144, 1999.

V. Meininger, et al., "Efficacy and safety of xaliproden in amyotrophic lateral sclerosis: results of two phase III trials", *ALS and other motor neuron disorders*, vol. 5, pp. 107-117, 2004.

L Lacomblez, et al., "Xaliproden in amyotrophic lateral sclerosis: early clinical trials", *ALS and other motor neuron disorders*, vol. 5, pp. 99-106, 2004.

MW Jann, "Buspirone: an update on a unique anxiolytic agent", *Pharmacotherapy*, vol. 8, No. 2, pp. 100-116, 1988.

BJ Turner, et al., "Opposing effects of low and high-dose clozapine on survival of transgenic amyotrophic lateral sclerosis mice", *Journal of Neuroscience Research*, vol. 74, pp. 605-613, 2003.

K Ohsugi, et al., "Lack of change in indoleamine metabolism in spinal cord of patients with amyotrophic lateral sclerosis", *Neuroscience Letters*, vol. 79, pp. 351-354, 1987.

M Damiano, et al., "Neural mitochondrial Ca$^{2+}$ capacity impairment precedes the onset of motor symptoms in G93A Cu/Zn-superoxide dismutase mutant mice", *Journal of Neurochemistry*, vol. 96, pp. 1349-1361, 2006.

E Sharifullina and A Nistri, "Glutamate uptake block triggers deadly rhythmic bursting of neonatal rat hypoglossal motoneurons", *J. Physiol.*, vol. 572.2, pp. 407-423, 2006.

M Tortarolo, et al., "Glutamate AMPA receptors change in motor neurons of SOD1$^{G93A}$ transgenic mice and their inhibition by a non-competitive antagonist ameliorates the progression of amytrophic lateral sclerosis-like disease", *Journal of Neuroscience Research*, vol. 83, pp. 134-146, 2006.

C Nishijima, et al., "Survival activity of troglitazone in rat motoneurones", *Journal of Neurochemistry*, vol. 76, pp. 383-390, 2001.

M Giannangeli, et al., "Effect of modifications of the alkylpiperazine moiety of trazodone on 5HT$_{2A}$ and $\alpha_1$ receptor binding affinity", *J. Med. Chem.*, vol. 42, pp. 336-345, 1999.

DN Middlemiss and JR Fozard, "8-Hydroxy-2-(DI-n-Propylamino)-Tetralin Discriminates Between Subtypes of the 5-HT$_1$ Recognition Site", *European Journal of Pharmacology*, vol. 90, pp. 151-153, 1983.

B Dean and W Hayes, "Decreased frontal cortical serotonin$_{2A}$ receptors in schizophrenia", *Schizophrenia Research*, vol. 21, pp. 133-139, 1996.

J Yamada, et al., "Pharmacological analysis of the variation in behavioural responses to tryptamine in five strains of mice", *European Journal of Pharmacology*, vol. 140, pp. 323-330, 1987.

J Yamada, et al., "The behavioural effects of intravenously administered tryptamine in mice", *Neuropharmacology*, vol. 26, No. 1, pp. 49-53, 1987.

Excerpt, *Bulletin of the Japanese Society for Neurochemistry*, vol. 44, No. 2 and 3, 2005.

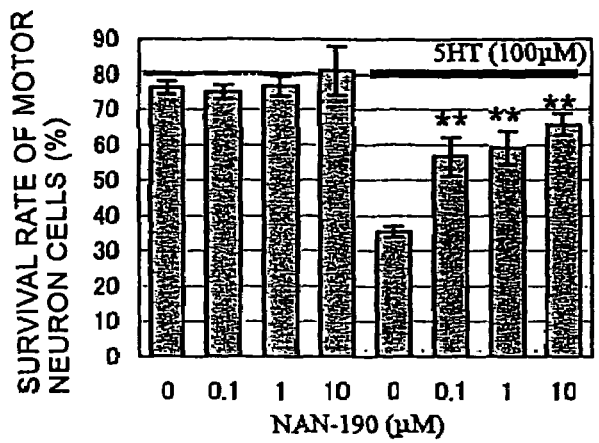
F I G. 2A
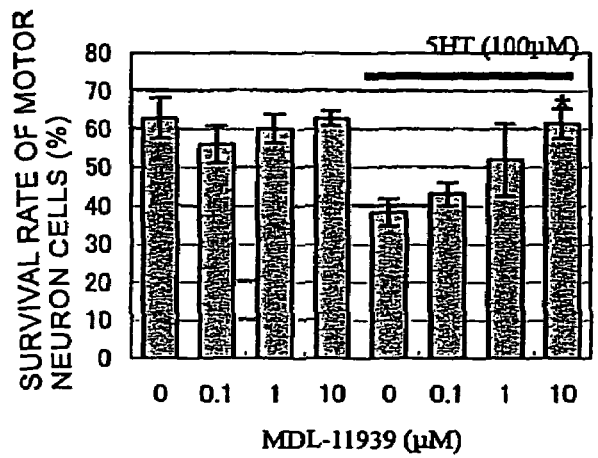
F I G. 2B
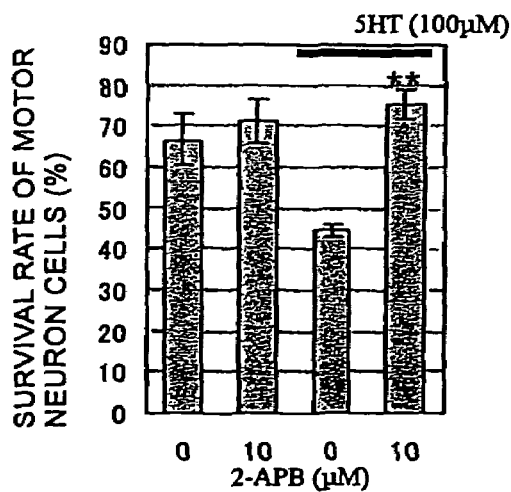
F I G. 3

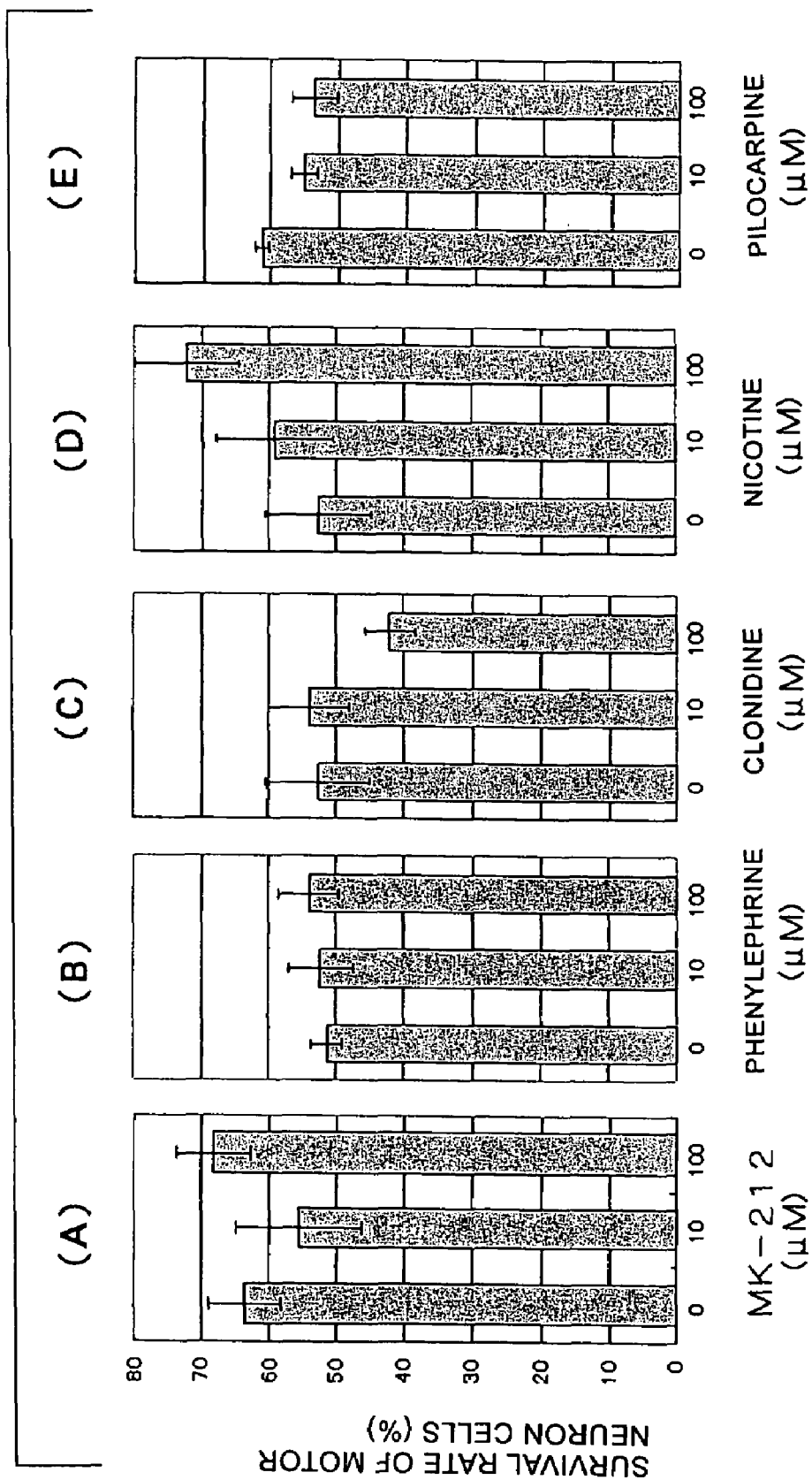
F I G. 4

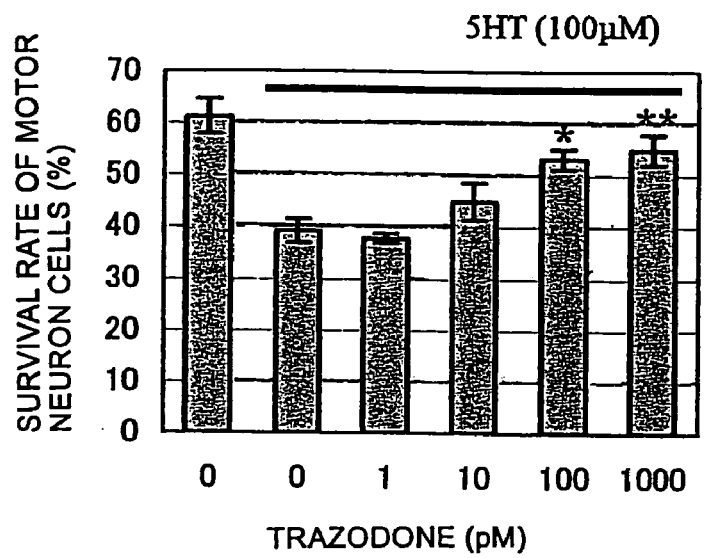
F I G. 5
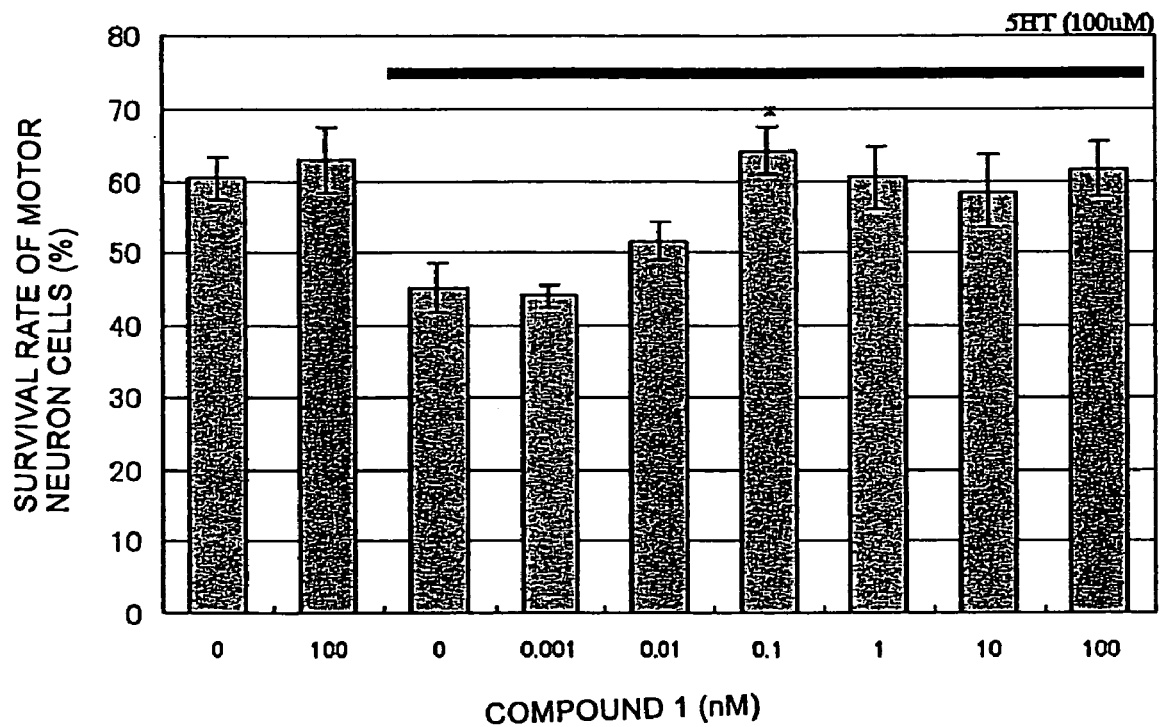
F I G. 6

METHOD FOR TREATING A MOTOR NEURON DISEASE

CROSS-REFERENCE TO RELATED APPLICATIONS

This application is entitled to the benefit of Provisional Patent Application Ser. No. 60/774,544, filed Feb. 21, 2006 and Provisional Patent Application Ser. No. 60/874,247, filed Dec. 12, 2006. The disclosure thereof in their entirety is incorporated herein by reference.

BACKGROUND OF THE INVENTION

1. Field of the Invention

The present invention relates to a method for treating a motor neuron disease. More particularly, the present invention relates to a method for treating a motor neuron disease, comprising the step of administering a therapeutically effective amount of a compound having serotonin receptor antagonist activity or its pharmacologically acceptable salt or their solvate optionally together with a pharmaceutically acceptable carrier to a mammal for which the treatment of said disease is indicated.

2. Background Technology

Amyotrophic lateral sclerosis (ALS) is a lethal progressive disease caused by selective degeneration and falling-off of motor neuron cells. The amyotrophic lateral sclerosis is mainly developed in adults in their 40s to 50s. In many cases, muscle weakening and amyotrophy in arm's periphery take place at the onset of ALS, the legs are then affected, and, two to six years after the manifestation of symptoms of bulbar paralysis, the patient dies. On the other hand, the patient's eye movement and sensory system and intellectual functions are maintained without any abnormality.

It is said that about 90% of ALS is accounted for by sporadic ALS that is not genetic in origin while the remainder is familial ALS that is genetic in origin. A 30 to 95% decrease in astroglial glutamate transporter EAAT2 (GLT-1) function is observed in 60 to 70% of the patients suffering from sporadic ALS. Further, abnormality is observed in RNA editing of EAAT2 in the ALS affected area (Lin et al. Neuron 20, 589-602 (1998); and Meyer et al. J. Neurol Sci 170, 45-50 (1999)). Mutation of superoxide dismutase 1 (SOD1), which detoxifies active oxygen, is observed in about 20% of the patients suffering from familial ALS (Deng et al. Science 261, 1047-51 (1993); and Rosen et al. Nature 362, 59-62 (1993)). Rats and mice transgenic for mutated SOD1 gene develop ALS-like symptoms (Nagai et al. J Neurosci 21, 9246-9254 (2001); and Gurney et al. Science 264, 1772-1775 (1994)) and thus have been widely used as ALS models. The pathogenic mechanism of ALS has not been fully elucidated yet (Rowland and Schneider, N Engl J Med 344, 1688-1700 (2001); and Julien, Cell 104, 581-591 (2001)). However, for example, glutamate excitotoxicity (Kawahara et al. Nature 427, 801 (2004); and Lipton, Nat Med 10, 347 (2004)) and oxidative stress (Rosen et al. Nature 362, 59-62 (1993); Cleveland and Rothstein, Nat Rev Neurosci 2, 806-819 (2001); Julien, Cell 104, 581-591 (2001); and Fryer et al. J Neurochem 72, 500-513 (1999)) have been considered as participating in the pathogenic mechanism.

Search for therapeutic agents has been conducted based on these hypothetical mechanisms. At the present time, however, any satisfactory therapeutic agent was not found by the search. Riluzole is the only approved therapeutic agent for ALS which is said to have glutamate release inhibitory activity. The therapeutic effect of Riluzole, however, is so small that Riluzole is unsatisfactory as a therapeutic agent (Bensimon, N Engl J Med 330, 585-591 (1994); and Lacomblez, Lancet 347, 1425-1431 (1996)). For Radicut considered as scavenging free radicals and protecting nerve cells, placebo control double blind tests have been conducted and proceeded to phase II. Various neurotrophic factors such as ciliary neurotrophic factor (CNTF), brain-derived neurotrophic factor (BDNF) and insulin-like growth factor-1 (IGF-1) inhibit cell death of motor neuron cells in in-vitro and in-vivo tests (Arakawa et al. J Neurosci 10, 3507-3515 (1990); Henderson et al. Curr Opin Neurobiol 2, 770-775 (1993); Ishii and Marsh, Exp Neurol 124, 96-99 (1993); Lewis et al. Exp Neurol 124, 73-88 (1993); Sendtner et al. J Neurol Sci 124 Suppl, 77-83 (1994); and Lindsay, Ciba Found Symp 196, 39-48, discussion 48-53 (1996)) and thus are expected as therapeutic agents for ALS, and clinical development of therapeutic agents has been conducted but failed to confirm survival advantage (Storkebaum et al. Nat Neurosci 8, 85-92 (2005); and Thoenen and Sendtner, Nat Neurosci 5 Suppl, 1046-1050 (2002)).

It is known that, as with a glutamate nervous system, a serotonin (5HT) nervous system applies excitatory stimuli to spinal motor neuron cells and is involved in the mechanism of the generation of plateau potential necessary for rhythmical motion, such as locomotion, and fictive locomotion (Hultborn and Kiehn, Curr Opin Neurobiol 2, 770-775 (1992); and Perrier and Hounsgaard, J Neurophysiol 89, 954-959 (2003)). For motor neuron cells, many data on the expression of four 5HT receptors, i.e., 5HT1A, 5HT1B, 5HT2A, and 5HT2C receptors, have been reported (Volgin et al. Eur J Neurosci 17, 1179-1188 (2003); and Ridet et al. J Neurosci Res 38, 109-121 (1994)). 5HT1A receptors excite motor neuron cells in the fetal phase (Hayashi et al. Brain Res Dev Brain Res 102, 21-33 (1997); and Wang and Dun, J Physiol 430, 87-103 (1990)), but on the other hand, after birth, the expression level of 5HT1A decreases (Talley et al. J Neurosci 17, 4473-4485 (1997)). It is known that the expression level of 5HT2A receptor increases with the growth thereof and, in mature motor neuron cells, the 5HT2A receptor is the main receptor for 5HT (Volgin et al. Eur J Neurosci 17, 1179-1188 (2003)). In particular, the 5HT2A receptor is known to regulate the rhythmical motion (M. Antri et al. Eur J Neurosci 16, 467-476 (2002)). There is a report that, in human autopsy samples, 5HT is present in a high concentration of 2 to 3 µM in a spinal ventral tissue, and, further, a tendency toward a further increase in the concentration of 5HT in autopsy samples of ALS patients has also been reported (Bertel et al. Brain Res 566, 54-60 (1991)). These reports demonstrate physiological importance of 5HT in motor function and suggest the participation of 5HT in selective falling-off of motor neuron cells in ALS.

There is a report that 5-hydroxytryptophan (5HTP), which is a 5HT precursor, prolongs the life of ALS model mice (Turner et al., Amyotroph Lateral Scler Other Motor Neuron Disord 4, 171-176 (2003)). In this report, however, 5HTP is peripherally administered and whether or not the concentration of 5HT in the brain is increased is not examined. Further, there is no description on the behavior of 5HT induction typified by head twitch. Accordingly, it has been regarded that there is a doubt about whether or not the prolongation of the life is derived from 5HT.

Clinical trials on the effect of some compounds having neuroprotective activity on ALS have been carried out. For example, SR57746A (Xaliproden) also acts agonistically on 5HT1A receptors and, in studies using cultured motor neuron cells, has been found to have neuroprotective activity (Iwasaki et al. J Neurol Sci 160 Suppl 1, S92-96 (1998); and Labie et al. Br J Pharmacol 127, 139-144 (1999)). A double blind placebo test has also been carried out (Meininger et al. Amyotroph Lateral Scler Other Motor Neuron Disord 5, 107-117 (2004); and Lacomblez et al. Amyotroph Lateral Scler Other Motor Neuron Disord 5, 99-106 (2004)). As a result, any clinically significant difference could not have been observed for life prolongation and delay of a deterioration in motor function although some tendency toward the development of this effect was confirmed. Buspirone, which has been found to have neuroprotective activity and is under clinical trials, is also a 5HT1A receptor agonist and is known as an antianxiety agent (Jann M W. Pharmacotherapy. 8(2), 100-116(1988)). These 5HT1A receptor agonists, however, have been studied aiming at clinical use through the utilization of the neuroprotective action, and the action thereof as 5HT1A receptor agonists has not been expected.

Clozapine, which is a third-generation therapeutic agent for schizophrenia, has also been found to have neuroprotective activity and has been reported to delay disordered walk function and death of ALS model mices (Turner et al. J Neurosci Res. 74, 605-613 (2003)). Clozapine is a compound which is selectively bound to 5HT2A receptors rather than D2 receptors (Naheed and Green, Neurosci Lett 79, 351-354 (2001)). In studies conducted by Turner et al., however, any observation of 5HT2A receptor has not been conducted, and the suppression of progress of ALS by taking advantage of 5HT2A receptor antagonist activity has not been expected. Further, administration at high dose has shortened survival time by contrast.

SUMMARY OF THE INVENTION

There is a demand for novel improved treatment method and pharmaceutical composition for motor neuron diseases (particularly ALS). An object of the present invention is to provide a treatment method and therapeutic agent for motor neuron diseases.

The present inventor has aimed, based on finding up to now, at the fact that, as with glutamate nerve fibers, serotonin nerve fibers provide excitatory input to motor neuron cells, and has made and tested a hypothesis that serotonin is involved in selective falling-off of motor neuron cells in motor neuron diseases, particularly ALS.

At the outset, serotonin was analyzed for excitotoxicity using a primary pure culture system of rat motor neuron cells. As a result, it was found that the serotonin has excitotoxicity comparable to glutamate and the toxicity is inhibited by compounds having serotonin receptor antagonist activity, particularly 5HT1A receptor antagonists and 5HT2A receptor antagonists.

The present inventor has further made and tested a hypothesis that IP3 receptors on endoplasmic reticula are involved as a downstream element of signals through 5HT2A receptors. As a result, it was found that IP3 receptor antagonists inhibit serotonin excitotoxicity, indicating the participation of 5HT2A receptors.

Up to now, there has been no report on the usefulness of compounds having serotonin receptor antagonist activity for motor neuron diseases. However, it has been surprisingly demonstrated that compounds having serotonin receptor antagonist activity, particularly 5HT1A receptor antagonists and 5HT2A receptor antagonists, can inhibit excessive excitation of motor neuron cells and can be therapeutic agents for motor neuron diseases, particularly therapeutic agents for ALS, that can inhibit neurodegeneration. The present invention has been made based on such finding.

According to the present invention, there is provided a method for treating a motor neuron disease, comprising the step of administering a therapeutically effective amount of a compound having serotonin receptor (particularly 5HT1A receptor and/or 5HT2A receptor) antagonist activity or its pharmacologically acceptable salt or their solvate optionally together with a pharmaceutically acceptable carrier to a mammal for which the treatment of said disease is indicated.

According to the present invention, there is provided a method for treating a motor neuron disease, comprising the step of selectively inhibiting a serotonin receptor (particularly a 5HT1A receptor and/or a 5HT2A receptor) in a mammal for which the treatment of said disease is indicated.

According to the present invention, there is provided a therapeutic agent for motor neuron diseases, comprising as an active ingredient a compound having serotonin receptor antagonist activity or its pharmacologically acceptable salt or their solvate.

BRIEF DESCRIPTION OF THE DRAWINGS

FIG. 1 is a diagram showing the results of evaluation of the toxicity of 5HT in a rat motor neuron primary pure culture system (mean±SEM (n =4)), wherein

FIG. 2 is a diagram showing the results of evaluation on the participation of 5HT1A and 5HT2A receptors in a rat motor neuron primary pure culture system in 5HT toxicity (mean±SEM (n=4), **$p<0.01$, and *$p<0.05$), wherein FIG. 2A shows the inhibition of 5HT toxicity by 5HT1A antagonist and FIG. 2B shows the inhibition of 5HT toxicity by 5HT2A antagonist.

FIG. 3 is a diagram showing the results of evaluation on the participation of IP3 receptor in a rat motor neuron primary pure culture system in 5HT toxicity (mean±SEM (n=4) and **$p<0.01$), demonstrating that IP3R antagonist inhibits 5HT toxicity.

FIG. 4 is a diagram showing the results of evaluation on the participation of various receptors in a rat motor neuron primary pure culture system in 5HT toxicity (mean±SEM (n=4)), wherein FIG. 4A shows data on 5HT2C receptor, FIG. 4B shows data on $\alpha 1$ receptor, FIG. 4C shows data on $\alpha 2$ receptor, FIG. 4D shows data on nicotinic Ach receptor, and FIG. 4E shows data on muscarinic Ach receptor.

FIG. 5 is a diagram showing 5HT toxicity inhibition effect attained by trazodone (mean±SEM (n=4), **$p<0.01$, and *$p<0.05$) in a rat motor neuron primary pure culture system.

FIG. 6 is a diagram showing the inhibitory effect of compound 1 against 5HT toxicity in a rat motor neuron primary pure culture system (mean±SEM (n=4) and *$p<0.05$).

DETAILED DESCRIPTION OF THE INVENTION

Figure 1A:
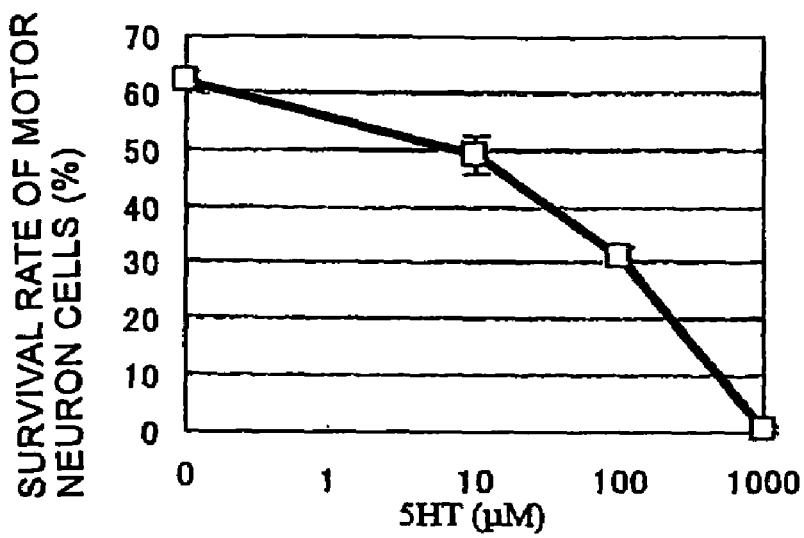
FIG. 1A shows the relationship between 5HT concentration and toxicity and FIG. 1B shows the comparison of 5HT toxicity with glutamate toxicity.

The present invention will be described in more detail. However, it should be noted that the following description is illustrative only and is not intended to limit the present invention to the following embodiments only. All of technical terms, scientific terms and professional terms used throughout the specification have the same meanings that are generally understood by those skilled in the technical field to which the invention belongs and they are intended to be used for the illustration of only a specific embodiment and are not intended to be limited thereto. The invention may be embodied in various forms without departing from the subject matter of the present invention.

All of prior art documents and laid-open publications, patent publications and other patent documents referred to in this specification are incorporated herein by reference and may be used for practicing the present invention.

Compounds having Serotonin Receptor Antagonist Activity

Compounds having serotonin receptor antagonist activity include, but are not limited to, for example, (i) compounds that act antagonistically against a binding reaction between a serotonin receptor and serotonin to inhibit the binding (serotonin receptor antagonists), and (ii) compounds that are bound directly to serotonin to inhibit binding between serotonin and a serotonin receptor. Among others, compounds having serotonin receptor antagonist function are preferred.

In the present invention, the serotonin receptor antagonist acts on the serotonin receptor to lower the intensity of signals generated from the receptor, to inhibit the generation of signals from the serotonin receptor, or to antagonize binding of agonist to the serotonin receptor. In the case of the serotonin receptor antagonist, the compound having serotonin receptor antagonist activity is not particularly limited and may have the so-called competitive antagonist activity or noncompetitive antagonist activity. Compounds, which can act antagonistically against a binding reaction between a 5HT1A receptor and serotonin to inhibit the binding (compounds having 5HT1A receptor antagonist activity), and compounds, which can act antagonistically against a binding reaction between a 5HT2A receptor and serotonin to inhibit the binding (compounds having 5HT2A receptor antagonist activity), are particularly preferred. Compounds having 5HT1A receptor antagonist activity may have 5HT2A receptor antagonist activity, and compounds having 5HT2A receptor antagonist activity may have 5HT1A receptor antagonist activity.

In the present invention, the expression "to inhibit the binding" means that the binding reaction is completely or partially inhibited and the degree of inhibition is not particularly limited. Preferably, however, the degree of binding reaction inhibition is not less than 10%, more preferably not less than 30%, still more preferably not less than 50%, still more preferably not less than 70%, particularly preferably not less than 80%, still particularly preferably not less than 90%, most preferably 100%.

For example, 1,4-substituted cyclic amine derivatives may be mentioned as the compound having serotonin receptor antagonist activity. Such derivatives include compounds represented by general formula (I) or their pharmacologically acceptable salts or their solvates:

[Chemical formula 1]

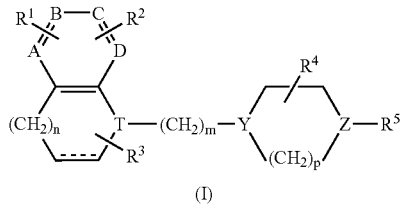

(I)

wherein

A, B, C, and D, which may be the same or different, represent methine or a nitrogen atom, provided that at least two of them represent methine, $\text{---}$ represents a single or double bond, T represents methine or a nitrogen atom, Y and Z, which may be the same or different, represent methine, a nitrogen atom, a group represented by the following formula

[Chemical formula 2]

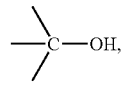

or a group represented by the following formula

[Chemical formula 3]

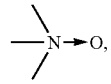

provided that at least one of them represent a nitrogen atom, $R^1$ and $R^2$, which may be the same or different, represent a hydrogen atom, a halogen atom, hydroxyl, $C_{1-6}$ alkylsulfonylamino $C_{1-6}$ alkyl, halogenated $C_{1-6}$ alkylsulfonylamino $C_{1-6}$ alkyl, 2-pyrrolidinon-1-yl, 1-hydroxy-1-(methoxypyridyl)methyl, methoxypyridylcarbonyl, 1,3-propanesultam-2-yl, hydroxypiperidylcarbonyl $C_{1-6}$ alkyl, hydroxy $C_{1-6}$ alkylamido $C_{1-6}$ alkyl, halogenated $C_{1-6}$ alkylamido $C_{1-6}$ alkyl, dihalogenated $C_{1-6}$ alkylamido $C_{1-6}$ alkyl, heteroarylamido $C_{1-6}$ alkyl, hydroxy $C_{1-6}$ alkylamido $C_{1-6}$ alkyl, optionally substituted amino, nitro, $C_{1-6}$ alkyl, $C_{1-6}$ alkoxy, $C_{1-6}$ acyl, $C_{1-6}$ alkoxy $C_{1-6}$ alkoxy, cyano, $C_{1-6}$ alkylsulfonyl, $C_{1-6}$ alkylsulfonylamido, hydroxy $C_{1-6}$ alkyl, hydroxy $C_{1-6}$ alkoxy, $C_{1-6}$ alkoxycarbonylamino, $C_{1-6}$ alkylsulfonylamino, N—$C_{1-6}$ alkyl $C_{1-6}$ alkylsulfonylamino, $C_{1-6}$ acylamino, optionally substituted amino $C_{1-6}$ alkyl, optionally N-substituted $C_{1-6}$ alkyl $C_{1-6}$ acylamino $C_{1-6}$ alkyl, optionally substituted aryl, optionally substituted arylsulfonylamino, $C_{1-6}$ alkylsulfonyloxy, hydroxyiminomethyl, (2-pyrrolidon-1-yl)methyl, (2-piperidon-1-yl)methyl, optionally substituted heteroaryl, optionally substituted aralkyl, optionally substituted heteroaryl $C_{1-6}$ alkyl, $C_{3-6}$ cycloalkylcarbonylamino $C_{1-6}$ alkyl, optionally substituted ureido, optionally substituted ureido $C_{1-6}$ alkyl, succinimide, (succinimido-1-yl) $C_{1-6}$ alkyl, amide, optionally substituted carbamoyl, optionally substituted carbamoyl $C_{1-6}$ alkyl, optionally substituted thiocarbamoyl $C_{1-6}$ alkyl, $C_{1-6}$ alkylaminothiocarbonylamino $C_{1-6}$ alkyl, formyl, arylcarbonyl, heteroarylcarbonyl, halogenated $C_{1-6}$ alkyl, (2-imidazolidinon-1-yl)methyl, (2,4-imidazolidinedion-3-yl)methyl, (2-oxazolidon-3-yl)methyl, (glutarimido-1-yl)methyl, optionally substituted heteroarylhydroxy $C_{1-6}$ alkyl, cyano $C_{1-6}$ alkyl, 1-hydroxy $C_{3-6}$ cycloalkyl, (2,4-thiazolidinedion-3-yl)methyl, optionally substituted 4-piperidylmethyl, aryl $C_{1-6}$ acyl, heteroaryl $C_{1-6}$ acyl, pyrrolidinylcarbonyl $C_{1-6}$ alkyl, optionally substituted aminosulfonyl $C_{1-6}$ alkyl, carboxy $C_{1-6}$ alkyl, or $C_{1-6}$ alkylamido $C_{1-6}$ alkyl, or alternatively $R^1$ and $R^2$ together may form an optionally substituted alicyclic ring, an optionally substituted heterocyclic ring, or alkylenedioxy, provided that these rings are optionally substituted, $R^3$ represents a hydrogen atom, a halogen atom, $C_{1-6}$ alkyl, hydroxyl, hydroxy $C_{1-6}$ alkyl, $C_{1-6}$ alkoxy, formyl, optionally substituted aralkyloxy, hydroxy $C_{1-6}$ alkoxy, optionally substituted sulfamoyl, or optionally N-substituted sulfamoyl $C_{1-6}$ alkyl, $R^4$ represents a hydrogen atom, $C_{1-6}$ alkyl, hydroxy $C_{1-6}$ alkyl, $C_{1-6}$ alkoxy $C_{1-6}$ alkyl, aryloxy $C_{1-6}$ alkyl in which the aryl group is optionally substituted, or aralkyloxy $C_{1-6}$ alkyl in which the aryl group is optionally substituted, $R^5$ represents $C_{1-6}$ alkyl, $C_{1-6}$ acyl, $C_{1-6}$ alkoxycarbonyl, arylcarbonyl, aryl $C_{1-6}$ acyl, or a group represented by the following formula $$-Q^1-(CH_2)_s-Q^2-R^6$$ [Chemical formula 4]

wherein both Q1 and Q2 represent a single bond, or any one of Q1 and Q2 is a single bond while the other represents an oxygen atom, carbonyl, a group represented by formula —NHCO—, a group represented by formula —NHSO$_2$—, or a group represented by formula >CH—$R^7$ wherein $R^7$ represents hydroxyl, $C_{1-6}$ alkyl, or a halogen atom, s is zero (0), or an integer of 1 to 6, $R^6$ represents a group selected from optionally substituted aryl, optionally substituted heteroaryl, or optionally substituted condensed heterocyclic group, n is zero (0) or an integer of 1 to 3, m is zero (0) or an integer of 1 to 6, and p is an integer of 1 to 3.

Preferably, all of A, B, C, and D represent methine.

Preferably, ═══ represents a double bond.

Preferably, T represents a nitrogen atom.

Preferably, Y represents methine, and Z represents a nitrogen atom.

Preferably, when one of $R^1$ and $R^2$ represents a hydrogen atom, the other substituent represents $C_{1-6}$ alkylsulfonylamino $C_{1-6}$ alkyl, $C_{1-6}$ alkoxy, optionally substituted carbamoyl, optionally substituted carbamoyl $C_{1-6}$ alkyl, $C_{1-6}$ alkylamido $C_{1-6}$ alkyl, or $C_{1-6}$ alkylaminothiocarbonylamino $C_{1-6}$ alkyl. More preferably, when one of $R^1$ and $R^2$ represents a hydrogen atom, the other substituent represents methylsulfonylaminomethyl, methoxy, carbamoyl optionally substituted by methyl, carbamoylmethyl optionally substituted by methyl, methylamidomethyl, or methylaminothiocarbonylaminomethyl.

Preferably, $R^3$ represents a hydrogen atom.

Preferably, $R^4$ represents a hydrogen atom.

Preferably, $R^5$ is represented by the following formula:

$$-Q^1-(CH_2)_s-Q^2-R^6$$ [Chemical formula 5]

wherein both $Q^1$ and $Q^2$ represent a single bond; s is 2; and $R^6$ represents optionally substituted aryl, optionally substituted heteroaryl, or an optionally substituted condensed heterocyclic group. More preferably, $R^6$ represents optionally substituted phenyl, optionally substituted pyridyl, optionally substituted quinolyl, optionally substituted chromanyl, optionally substituted benzoxazolyl, optionally substituted benzisoxazolyl, or benzo[1,4]dioxanyl.

Preferably, n is zero (0).

Preferably, m is zero (0).

Preferably, p is 2.

In a preferred embodiment of the therapeutic agent according to the present invention, the therapeutic agent comprises a compound represented by formula (I) wherein all of A, B, C, and D represent methine; ═══ represents a double bond; T represents a nitrogen atom; Y represents methine; Z represents a nitrogen atom; when one of $R^1$ and $R^2$ represents a hydrogen atom, the other substituent represents $C_{1-6}$ alkylsulfonylamino $C_{1-6}$ alkyl, $C_{1-6}$ alkoxy, optionally substituted carbamoyl, optionally substituted carbamoyl $C_{1-6}$ alkyl, $C_{1-6}$ alkylamido $C_{1-6}$ alkyl, or $C_{1-6}$ alkylaminothiocarbonylamino $C_{1-6}$ alkyl; $R^3$ represents a hydrogen atom; $R^4$ represents a hydrogen atom; $R^5$ is represented by the following formula:

$$-Q^1-(CH_2)_s-Q^2-R^6$$ [Chemical formula 6]

wherein both $Q^1$ and $Q^2$ represent a single bond, s is 2, $R^6$ represents optionally substituted aryl, optionally substituted heteroaryl, or optionally substituted condensed heterocyclic group; m is zero (0); n is zero (0); and p is 2.

In a more preferred embodiment of the therapeutic agent according to the present invention, the therapeutic agent comprises a compound represented by formula (I) wherein all of A, B, C, and D represent methine; ═══ represents a double bond; T represents a nitrogen atom; Y represents methine; Z represents a nitrogen atom; when one of $R^1$ and $R^2$ represents a hydrogen atom, the other substituent represents methylsulfonylaminomethyl, methoxy, carbamoyl optionally substituted by methyl, carbamoylmethyl optionally substituted by methyl, methylamidomethyl, or methylaminothiocarbonylamino methyl; $R^3$ represents a hydrogen atom; $R^4$ represents a hydrogen atom; $R^5$ is represented by the following formula:

$$-Q^1-(CH_2)_s-Q^2-R^6$$ [Chemical formula 7]

wherein both $Q^1$ and $Q^2$ represent a single bond, s is 2, $R^6$ represents optionally substituted phenyl, optionally substituted pyridyl, optionally substituted quinolyl, optionally substituted chromanyl, optionally substituted benzoxazolyl, optionally substituted benzisoxazolyl, or benzo[1,4]dioxanyl; m is zero (0); n is zero (0); and p is 2.

Additional 1,4-substituted cyclic amine derivatives having serotonin receptor antagonist activity include compounds represented by general formula (II) or their pharmacologically acceptable salts or their solvates:

[Chemical formula 8]

(II)

wherein

Ra represents a hydrogen atom, a halogen atom, hydroxyl, $C_{1-6}$ alkylsulfonylamino $C_{1-6}$ alkyl, halogenated $C_{1-6}$ alkylsulfonylamino $C_{1-6}$ alkyl, 2-pyrrolidinon-1-yl, 1-hydroxy-1-(methoxypyridyl)methyl, methoxypyridylcarbonyl, 1,3-propanesultam-2-yl, hydroxypiperidylcarbonyl $C_{1-6}$ alkyl, hydroxy $C_{1-6}$ alkylamido $C_{1-6}$ alkyl, halogenated $C_{1-6}$ alkylamido $C_{1-6}$ alkyl, dihalogenated $C_{1-6}$ alkylamido $C_{1-6}$ alkyl, heteroarylamido $C_{1-6}$ alkyl, hydroxy $C_{1-6}$ alkylamido $C_{1-6}$ alkyl, optionally substituted amino, nitro, $C_{1-6}$ alkyl, $C_{1-6}$ alkoxy, $C_{1-6}$ acyl, $C_{1-6}$ alkoxy $C_{1-6}$ alkoxy, cyano, $C_{1-6}$ alkylsulfonyl, $C_{1-6}$ sulfonylamido, hydroxy $C_{1-6}$ alkyl, hydroxy $C_{1-6}$ alkoxy, $C_{1-6}$ alkoxycarbonylamino, $C_{1-6}$ alkylsulfonylamino, N—$C_{1-6}$ alkyl $C_{1-6}$ alkylsulfonylamino, $C_{1-6}$ acylamino, optionally substituted amino $C_{1-6}$ alkyl, optionally N-substituted $C_{1-6}$ alkyl $C_{1-6}$ acylamino $C_{1-6}$ alkyl, optionally substituted aryl, optionally substituted arylsulfonylamino, $C_{1-6}$ alkylsulfonyloxy, hydroxyiminomethyl, (2-pyrrolidon-1-yl)methyl, (2-piperidon-1-yl)methyl, optionally substituted heteroaryl, optionally substituted aralkyl, optionally substituted heteroaryl $C_{1-6}$ alkyl, $C_{3-6}$ cycloalkylcarbonylamino $C_{1-6}$ alkyl, optionally substituted ureido, optionally substituted ureido $C_{1-6}$ alkyl, succinimide, (succinimido-1-yl)$C_{1-6}$ alkyl, amide, optionally substituted carbamoyl, optionally substituted carbamoyl $C_{1-6}$ alkyl, optionally substituted thiocarbamoyl $C_{1-6}$ alkyl, $C_{1-6}$ alkylaminothiocarbonylamino $C_{1-6}$ alkyl, formyl, aryl $C_{1-6}$ acyl, arylcarbonyl, heteroarylcarbonyl, halogenated $C_{1-6}$ alkyl, (2-imidazolidinon-1-yl)methyl, (2,4-imidazolidinedion-3-yl)methyl, (2-oxazolidon-3-yl)methyl, (glutarimido-1-yl)methyl, optionally substituted heteroarylhydroxyalkyl, cyano $C_{1-6}$ alkyl, 1-hydroxy $C_{3-6}$ cycloalkyl, (2,4-thiazolidinedion-3-yl)methyl, optionally substituted 4-piperidylmethyl, heteroaryl $C_{1-6}$ acyl, pyrrolidinylcarbonyl $C_{1-6}$ alkyl, optionally substituted aminosulfonyl $C_{1-6}$ alkyl, carboxy $C_{1-6}$ alkyl, or $C_{1-6}$ alkylamido $C_{1-6}$ alkyl, Rb represents optionally substituted aryl, optionally substituted heteroaryl, or an optionally substituted condensed heterocyclic group, and ═ represents a single bond or a double bond.

Preferably, Ra represents $C_{1-6}$ alkylsulfonylamino $C_{1-6}$ alkyl, $C_{1-6}$ alkoxy, optionally substituted carbamoyl, optionally substituted carbamoyl $C_{1-6}$ alkyl, $C_{1-6}$ alkylamido $C_{1-6}$ alkyl, or $C_{1-6}$ alkylaminothiocarbonylamino $C_{1-6}$ alkyl. More preferably, Ra represents methylsulfonylaminomethyl, methoxy, carbamoyl optionally substituted by methyl, carbamoylmethyl optionally substituted by methyl, methylamidomethyl, or methylaminothiocarbonylamino methyl.

Preferably, Rb represents optionally substituted phenyl, optionally substituted pyridyl, optionally substituted quinolyl, optionally substituted chromanyl, optionally substituted benzoxazolyl, optionally substituted benzisoxazolyl, or benzo[1,4]dioxanyl.

Preferably, ═ represents a double bond.

In a preferred embodiment of the therapeutic agent according to the present invention, the therapeutic agent comprises a compound represented by formula (II) wherein Ra represents $C_{1-6}$ alkylsulfonylaminoalkyl, $C_{1-6}$ alkoxy, optionally substituted carbamoyl, optionally substituted carbamoyl $C_{1-6}$ alkyl, $C_{1-6}$ alkylamidoalkyl, or $C_{1-6}$ alkylaminothiocarbonylamino $C_{1-6}$ alkyl; Rb represents optionally substituted phenyl, optionally substituted pyridyl, optionally substituted quinolyl, optionally substituted chromanyl, optionally substituted benzoxazolyl, optionally substituted benzisoxazolyl, or benzo[1,4]dioxanyl; and ═ represents a double bond.

In a more preferred embodiment of the therapeutic agent according to the present invention, the therapeutic agent comprises a compound represented by formula (II) wherein Ra represents methylsulfonylaminomethyl, methoxy, carbamoyl optionally substituted by methyl, carbamoylmethyl optionally substituted by methyl, methylamidomethyl, or methylaminothiocarbonylaminomethyl; Rb represents optionally substituted phenyl, optionally substituted pyridyl, optionally substituted quinolyl, optionally substituted chromanyl, optionally substituted benzoxazolyl, optionally substituted benzisoxazolyl, or benzo[1,4]dioxanyl; and ═ represents a double bond.

Additional 1,4-substituted cyclic amine derivatives having serotonin receptor antagonist activity include compounds represented by general formula (III) or their pharmacologically acceptable salts or their solvates:

[Chemical formula 9]

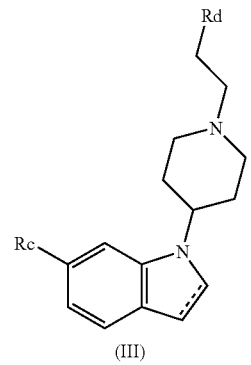

(III)

wherein

Rc represents $C_{1-6}$ alkylsulfonylamino $C_{1-6}$ alkyl, $C_{1-6}$ alkoxy, optionally substituted carbamoyl, optionally substituted carbamoyl $C_{1-6}$ alkyl, $C_{1-6}$ alkylamido $C_{1-6}$ alkyl, or $C_{1-6}$ alkylaminothiocarbonylamino $C_{1-6}$ alkyl, Rd represents phenyl optionally having one to four substituents selected from the following substituent group A1, or substituted phenyl in which two adjacent substituents, together with two carbon atoms to which they are attached, form a five- to seven-membered ring non-aromatic hydrocarbocyclic group, a five- to seven-membered ring non-aromatic heterocyclic group, a six-membered ring aromatic hydrocarbocyclic group, or a five- or six-membered ring aromatic heterocyclic group, which may be substituted by one to four substituents selected from the following substituent group B1, wherein said substituent group A1 consists of (1) a hydrogen atom, (2) a halogen atom, (3) cyano, (4) hydroxyl, (5) nitro, (6) carboxyl, (7) $C_{3-8}$ cycloalkyl, (8) $C_{2-6}$ alkenyl, (9) $C_{2-6}$ alkynyl, (10) $C_{1-6}$ alkylthio, (11) $C_{1-6}$ alkoxycarbonyl, (12) $C_{1-6}$ alkylsulfonyl, (13) $C_{1-6}$ alkyl optionally substituted by one to three substituents selected from the group consisting of a halogen atom, hydroxyl and $C_{1-6}$ alkoxy, (14) $C_{1-6}$ alkoxy optionally substituted by one to three halogen atoms, (15) amino optionally substituted by a substituent selected from the group consisting of $C_{1-6}$ alkyl, formyl, $C_{1-6}$ alkanoyl and $C_{1-6}$ alkylsulfonyl, and (16) carbamoyl optionally substituted by one or two $C_{1-6}$ alkyls, and said substituent group B1 consists of (1) a hydrogen atom, (2) a halogen atom, (3) cyano, (4) hydroxyl, (5) nitro, (6) oxo, (7) carboxyl, (8) $C_{3-8}$ cycloalkyl, (9) $C_{2-6}$ alkenyl, (10) $C_{2-6}$ alkynyl, (11) $C_{1-6}$ alkylthio, (12) $C_{1-6}$ alkoxycarbonyl, (13) $C_{1-6}$ alkylsulfonyl, (14) $C_{1-6}$ alkyl optionally substituted by a halogen atom, hydroxyl and $C_{1-6}$ alkoxy, (15) $C_{1-6}$ alkoxy optionally substituted by one to three halogen atoms, (16) amino optionally substituted by a substituent selected from the group consisting of $C_{1-6}$ alkyl, formyl, $C_{1-6}$ alkanoyl and $C_{1-6}$ alkylsulfonyl, (17) carbamoyl optionally substituted by one or two $C_{1-6}$ alkyls, (18) $C_{1-6}$ alkoxyimino, (19) $C_{5-6}$ cycloalkyl formed by two $C_{1-3}$ alkyls attached to the same carbon atom, and (20) tetrahydropyranyl formed by two $C_{1-3}$ alkyls attached to the same carbon atom, together with an oxygen atom and the carbon atom, and ═ represents a single bond or a double bond.

Preferably, Rc represents methylsulfonylaminomethyl, methoxy, carbamoyl optionally substituted by methyl, carbamoylmethyl optionally substituted by methyl, methylamidomethyl, or methylaminothiocarbonylamino methyl.

Preferably, Rd represents phenyl substituted by a halogen atom.

Preferably, Rd represents substituted phenyl in which adjacent substituents, which together with two carbon atoms to which they are attached, form a group represented by the following formula:

[Chemical formula 10]

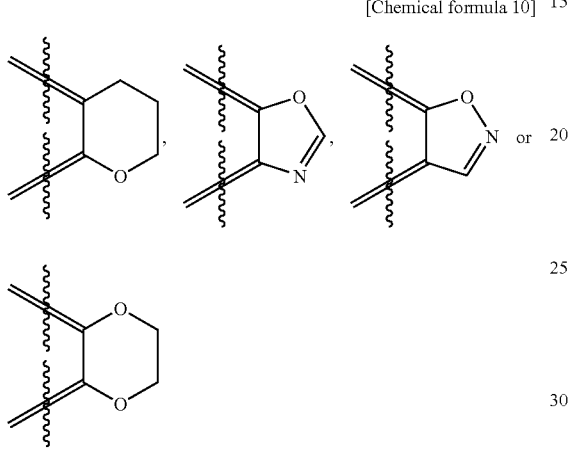

wherein hydrogen atoms on each cyclic group are optionally substituted by one to four substituents selected from the following substituent group B1.

The substituent group B1 consists of (1) a hydrogen atom, (2) a halogen atom, (3) cyano, (4) hydroxyl, (5) nitro, (6) oxo, (7) carboxyl, (8) $C_{3-8}$ cycloalkyl, (9) $C_{2-6}$ alkenyl, (10) $C_{2-6}$ alkynyl, (11) $C_{1-6}$ alkylthio, (12) $C_{1-6}$ alkoxycarbonyl, (13) $C_{1-6}$ alkylsulfonyl, (14) $C_{1-6}$ alkyl optionally substituted by a halogen atom, hydroxyl and $C_{1-6}$ alkoxy, (15) $C_{1-6}$ alkoxy optionally substituted by one to three halogen atoms, (16) amino optionally substituted by a substituent selected from the group consisting of $C_{1-6}$ alkyl, formyl, $C_{1-6}$ alkanoyl and $C_{1-6}$ alkylsulfonyl, (17) carbamoyl optionally substituted by one or two $C_{1-6}$ alkyls, (18) $C_{1-6}$ alkoxyimino, (19) $C_{5-6}$ cycloalkyl formed by two $C_{1-3}$ alkyls attached to the same carbon atom, and (20) tetrahydropyranyl formed by two $C_{1-3}$ alkyls attached to the same carbon atom, together with an oxygen atom and the carbon atom.

Preferably, ═══ represents a double bond.

In a preferred embodiment of the therapeutic agent according to the present invention, the therapeutic agent comprises a compound represented by formula (III) wherein Rc represents methylsulfonylaminomethyl, methoxy, carbamoyl optionally substituted by methyl, carbamoylmethyl optionally substituted by methyl, methylamidomethyl, or methylaminothiocarbonylamino methyl; and Rd represents phenyl substituted by a halogen atom, or substituted phenyl in which adjacent substituents, which together with two carbon atoms to which they are attached, form a group represented by the following formula:

[Chemical formula 11]

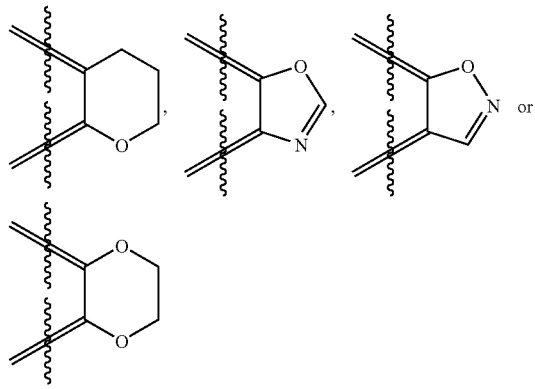

wherein hydrogen atoms on each cyclic group are optionally substituted by one to four substituents selected from the following substituent group B1.

The substituent group B1 consists of (1) a hydrogen atom, (2) a halogen atom, (3) cyano, (4) hydroxyl, (5) nitro, (6) oxo, (7) carboxyl, (8) $C_{3-8}$ cycloalkyl, (9) $C_{2-6}$ alkenyl, (10) $C_{2-6}$ alkynyl, (11) $C_{1-6}$ alkylthio, (12) $C_{1-6}$ alkoxycarbonyl, (13) $C_{1-6}$ alkylsulfonyl, (14) $C_{1-6}$ alkyl optionally substituted by a halogen atom, hydroxyl and $C_{1-6}$ alkoxy, (15) $C_{1-6}$ alkoxy optionally substituted by one to three halogen atoms, (16) amino optionally substituted by a substituent selected from the group consisting of $C_{1-6}$ alkyl, formyl, $C_{1-6}$ alkanoyl and $C_{1-6}$ alkylsulfonyl, (17) carbamoyl optionally substituted by one or two $C_{1-6}$ alkyls, (18) $C_{1-6}$ alkoxyimino, (19) $C_{5-6}$ cycloalkyl formed by two $C_{1-3}$ alkyls attached to the same carbon atom, and (20) tetrahydropyranyl formed by two $C_{1-3}$ alkyls attached to the same carbon atom, together with an oxygen atom and the carbon atom; and ═══ represents a double bond.

Further additional examples of 1,4-substituted cyclic amine derivatives having serotonin receptor antagonist activity include compounds represented by general formula (IV) or their pharmacologically acceptable salts or their solvates:

[Chemical formula 12]

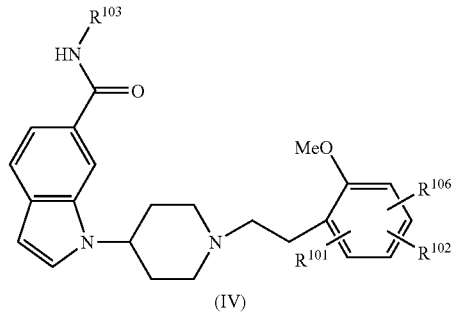

(IV)

wherein $R^{101}$ and $R^{102}$ are mutually adjacent substituents which, together with two carbon atoms to which they are attached, form (1) a five- to seven-membered ring non-aromatic hydrocarbocyclic group, (2) a five- to seven-membered ring non-aromatic heterocyclic group, (3) a six-membered ring aromatic hydrocarbocyclic group, or (4) a five- or six-membered ring aromatic heterocyclic group, which may be substituted by 1 to 4 substituents selected from the following substituent group B1, $R^{103}$ represents a hydrogen atom or methyl, $R^{106}$ represents a substituent selected from the following substituent group A1, said substituent group A1 consists of (1) a hydrogen atom, (2) a halogen atom, (3) cyano, (4) hydroxyl, (5) nitro, (6) carboxyl, (7) $C_{3-8}$ cycloalkyl, (8) $C_{2-6}$ alkenyl, (9) $C_{2-6}$ alkynyl, (10) $C_{1-6}$ alkylthio, (11) $C_{1-6}$ alkoxycarbonyl, (12) $C_{1-6}$ alkylsulfonyl, (13) $C_{1-6}$ alkyl optionally substituted by one to three substituents selected from the group consisting of a halogen atom, hydroxyl and $C_{1-6}$ alkoxy, (14) $C_{1-6}$ alkoxy optionally substituted by one to three halogen atoms, (15) amino optionally substituted by a substituent selected from the group consisting of $C_{1-6}$ alkyl, formyl, $C_{1-6}$ alkanoyl and $C_{1-6}$ alkylsulfonyl, and (16) carbamoyl optionally substituted by one or two $C_{1-6}$ alkyls, and said substituent group B1 consists of (1) a hydrogen atom, (2) a halogen atom, (3) cyano, (4) hydroxyl, (5) nitro, (6) oxo, (7) carboxyl, (8) $C_{3-8}$ cycloalkyl, (9) $C_{2-6}$ alkenyl, (10) $C_{2-6}$ alkynyl, (11) $C_{1-6}$ alkylthio, (12) $C_{1-6}$ alkoxycarbonyl, (13) $C_{1-6}$ alkylsulfonyl, (14) $C_{1-6}$ alkyl optionally substituted by a halogen atom, hydroxyl and $C_{1-6}$ alkoxy, (15) $C_{1-6}$ alkoxy optionally substituted by one to three halogen atoms, (16) amino optionally substituted by a substituent selected from the group consisting of $C_{1-6}$ alkyl, formyl, $C_{1-6}$ alkanoyl and $C_{1-6}$ alkylsulfonyl, (17) carbamoyl optionally substituted by one or two $C_{1-6}$ alkyls, (18) $C_{1-6}$ alkoxyimino, (19) $C_{5-6}$ cycloalkyl formed by two $C_{1-3}$ alkyls attached together to the same carbon atom, and (20) tetrahydropyranyl formed by two $C_{1-3}$ alkyls attached to the same carbon atom, together with an oxygen atom and the carbon atom.

Preferably, $R^{101}$ and $R^{102}$ are mutually adjacent substituents which, together with two carbon atoms to which they are attached, form a group represented by the following formula:

[Chemical formula 13]

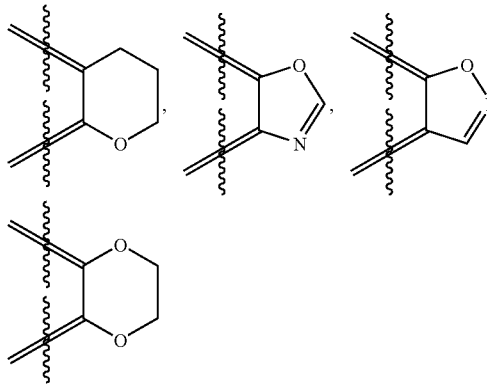

wherein hydrogen atoms on each cyclic group are optionally substituted by one to four substituents selected from the following substituent group B1.

The substituent group B1 consists of (1) a hydrogen atom, (2) a halogen atom, (3) cyano, (4) hydroxyl, (5) nitro, (6) oxo, (7) carboxyl, (8) $C_{3-8}$ cycloalkyl, (9) $C_{2-6}$ alkenyl, (10) $C_{2-6}$ alkynyl, (11) $C_{1-6}$ alkylthio, (12) $C_{1-6}$ alkoxycarbonyl, (13) $C_{1-6}$ alkylsulfonyl, (14) $C_{1-6}$ alkyl optionally substituted by a halogen atom, hydroxyl and $C_{1-6}$ alkoxy, (15) $C_{1-6}$ alkoxy optionally substituted by one to three halogen atoms, (16) amino optionally substituted by a substituent selected from the group consisting of $C_{1-6}$ alkyl, formyl, $C_{1-6}$ alkanoyl and $C_{1-6}$ alkylsulfonyl, (17) carbamoyl optionally substituted by one or two $C_{1-6}$ alkyls, (18) $C_{1-6}$ alkoxyimino, (19) $C_{5-6}$ cycloalkyl formed by two $C_{1-3}$ alkyls attached to the same carbon atom, and (20) tetrahydropyranyl formed by two $C_{1-3}$ alkyls attached to the same carbon atom, together with an oxygen atom and the carbon atom.

Preferably, $R^{106}$ is unsubstituted.

In a preferred embodiment of the present invention, the therapeutic agent comprises a compound represented by formula (IV) wherein $R^{101}$ and $R^{102}$ are mutually adjacent substituents which, together with two carbon atoms to which they are attached, form a group represented by the following formula:

[Chemical formula 14]

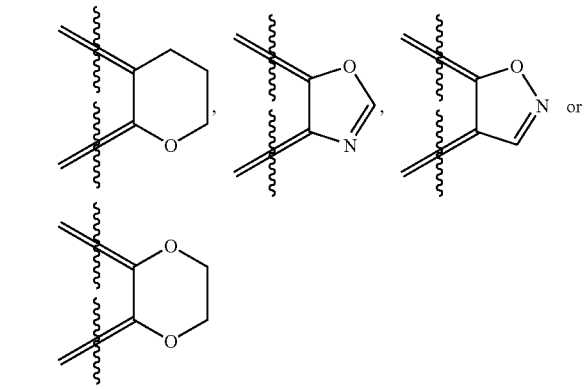

wherein hydrogen atoms on each cyclic group are optionally substituted by one to four substituents selected from the following substituent group B1.

The substituent group B1 consists of (1) a hydrogen atom, (2) a halogen atom, (3) cyano, (4) hydroxyl, (5) nitro, (6) oxo, (7) carboxyl, (8) $C_{3-8}$ cycloalkyl, (9) $C_{2-6}$ alkenyl, (10) $C_{2-6}$ alkynyl, (11) $C_{1-6}$ alkylthio, (12) $C_{1-6}$ alkoxycarbonyl, (13) $C_{1-6}$ alkylsulfonyl, (14) $C_{1-6}$ alkyl optionally substituted by a halogen atom, hydroxyl and $C_{1-6}$ alkoxy, (15) $C_{1-6}$ alkoxy optionally substituted by one to three halogen atoms, (16) amino optionally substituted by a substituent selected from the group consisting of $C_{1-6}$ alkyl, formyl, $C_{1-6}$ alkanoyl and $C_{1-6}$ alkylsulfonyl, (17) carbamoyl optionally substituted by one or two $C_{1-6}$ alkyls, (18) $C_{1-6}$ alkoxyimino, (19) $C_{5-6}$ cycloalkyl formed by two $C_{1-3}$ alkyls attached to the same carbon atom, and (20) tetrahydropyranyl formed by two $C_{1-3}$ alkyls attached to the same carbon atom, together with an oxygen atom and the carbon atom; and $R^{106}$ is unsubstituted.

In formulae (I), (II), (III), and (IV), the halogen atom is a chlorine atom, a fluorine atom, a bromine atom, or an iodine atom, preferably a chlorine atom, a fluorine atom, or a bromine atom.

In formulae (I) and (II), the optionally substituted amino more specifically refers to amino, and amino substituted, for example, by $C_{1-6}$ alkyl or optionally substituted aryl.

In formulae (I), (II), (III), and (IV), the term "$C_{1-6}$ alkyl" refers to alkyl having 1 to 6 carbon atoms (preferably 1 to 4 carbon atoms), and preferred examples thereof include straight chain or branched chain alkyls, for example, methyl, ethyl, n-propyl, isopropyl, n-butyl, isobutyl, sec-butyl, tert-butyl, n-pentyl, isopentyl, neopentyl, tert-pentyl, n-hexyl, 1-methylpropyl, 1,2-dimethylpropyl, 2-ethylpropyl, 1-methyl-2-ethylpropyl, 1-ethyl-2-methylpropyl, 1,1,2-trimethylpropyl, 1-methylbutyl, 2-methylbutyl, 1,1-dimethylbutyl, 2,2-dimethylbutyl, 2-ethylbutyl, 1,3-dimethylbutyl, 2-methylpentyl, and 3-methylpentyl.

In formulae (I), (II), (III), and (IV), the term "$C_{1-6}$ alkoxy" refers to such a group that a hydrogen atom in alkyl having 1 to 6 carbon atoms (preferably 1 to 4 carbon atoms) has been substituted by an oxygen atom, and preferred examples thereof include methoxy, ethoxy, n-propoxy, isopropoxy, sec-propoxy, n-butoxy, isobutoxy, sec-butoxy, tert-butoxy, n-pentyloxy, isopentyloxy, sec-pentyloxy, tert-pentyloxy, n-hexyloxy, isohexyloxy, 1,2-dimethylpropoxy, 2-ethylpropoxy, 1-methyl-2-ethylpropoxy, 1-ethyl-2-methylpropoxy, 1,1,2-trimethylpropoxy, 1,1-dimethylbutoxy, 2,2-dimethylbutoxy, 2-ethylbutoxy, 1,3-dimethylbutoxy, 2-methylpentyloxy, 3-methylpentyloxy, and hexyloxy.

In formulae (I), (II), (III), and (IV), the term "$C_{1-6}$ alkanoyl" (synonymous with $C_{1-6}$ alkylcarbonyl or $C_{1-6}$ acyl) refers to such a group that one hydrogen atom in alkyl having 1 to 6 carbon atoms (preferably 1 to 4 carbon atoms) has been substituted by carbonyl, and preferred examples thereof include acetyl, propionyl, and butyryl.

In formulae (I), (II), (III), and (IV), the term "$C_{1-6}$ alkylsulfonyl" refers to such a group that one hydrogen atom in alkyl having 1 to 6 carbon atoms (preferably 1 to 4 carbon atoms) has been substituted by sulfonyl, and preferred examples thereof include methanesulfonyl and ethanesulfonyl.

In formulae (I), (II), (III), and (IV), the term "$C_{1-6}$ alkoxycarbonyl" refers to such a group that carbonyl has been attached to the above-described alkoxy, and preferred examples thereof include methoxycarbonyl and ethoxycarbonyl.

In formulae (I), (II), and (III), more specific examples of $C_{1-6}$ alkylsulfonylamino include such groups that sulfonylamino (—SO$_2$N<) has been attached to the above $C_{1-6}$ alkyl, for example, methanesulfonylamino, ethanesulfonylamino, propanesulfonylamino, butanesulfonylamino, and N-methylmethanesulfonylamino.

In formulae (I) and (II), the term "$C_{3-6}$ cycloalkyl" refers to cyclic alkyl having 3 to 6 carbon atoms, and preferred examples thereof include cyclopropyl, cyclobutyl, cyclopentyl, and cyclohexyl.

In formulae (I) and (II), more specific examples of $C_{1-6}$ alkoxyalkoxy include such groups that the above-described $C_{1-6}$ alkoxy has been further substituted by $C_{1-6}$ alkoxy, for example, methoxymethoxy, methoxyethoxy, and methoxypropoxy; more specific examples of sulfonylamido include a group represented by formula (—SO$_2$NH$_2$); more specific examples of hydroxy $C_{1-6}$ alkyl include such groups that the above-described $C_{1-6}$ alkyl has been substituted by one or more hydroxys, for example, hydroxymethyl, hydroxyethyl, and hydroxypropyl; more specific examples of $C_{1-6}$ acylamino include amino to which a $C_{1-6}$ fatty acid having 2 to 6 carbon atoms has been attached, for example, acetamide, propionamide, and butyrylamide.

In formulae (I) and (II), more specific examples of optionally N-substituted $C_{1-6}$ acylaminoalkyl include such groups that the above-described $C_{1-6}$ acyl has been attached to amino $C_{1-6}$ alkyl, for example, acetamidomethyl, acetamidoethyl, propionamidomethyl, and butyrylamidomethyl. In this case, the nitrogen atom is optionally further substituted, for example, by $C_{1-6}$ alkyl.

In formulae (I) and (II), more specific examples of optionally substituted arylsulfonylamino include such groups that sulfonylamino (—SO$_2$NH—) has been attached to aryl, or such substituted aryl has been further substituted, for example, benzenesulfonylamino and toluenesulfonylamino; more specific examples of $C_{1-6}$ alkylsulfonyloxy include such groups that sulfonyloxy (—SO$_3$—) has been attached to the above-described $C_{1-6}$ alkyl; and more specific examples of optionally substituted aminoalkyl include such groups that amino has been attached to the above-described $C_{1-6}$ alkyl. In this case, the nitrogen atom is optionally further substituted, for example, by $C_{1-6}$ alkyl or $C_{1-6}$ alkylsulfonyl.

In formulae (I) and (II), more specific examples of optionally substituted aryl include phenyl and naphthyl, or substituted phenyl and naphthyl. Here, preferred substituents include halogen atoms and $C_{1-6}$ alkoxy. More preferred are a fluorine atom, a chlorine atom, and methoxy. The substituents may be the same or different, and the presence of a plurality of substituents is possible.

In formulae (I) and (II), more specific examples of optionally substituted heteroaryl include optionally substituted pyridyl, optionally substituted pyrazyl, optionally substituted pyrimidyl, optionally substituted pyrrolyl, optionally substituted imidazolyl, optionally substituted pyrazolyl, optionally substituted furyl, optionally substituted thienyl, and optionally substituted thiazolyl. Here, preferred substituents include halogen atoms and $C_{1-6}$ alkoxy. More preferred are a fluorine atom, a chlorine atom, and methoxy. The substituents may be the same or different, and the presence of a plurality of substituents is possible.

In formulae (I) and (II), more specific examples of optionally substituted aralkyl include optionally substituted benzyl, optionally substituted phenethyl and optionally substituted phenylpropyl; more specific examples of optionally substituted heteroarylalkyl include optionally substituted pyridylmethyl, optionally substituted pyridylethyl, optionally substituted pyrazylethyl, optionally substituted pyridonemethyl, optionally substituted pyrrolidonemethyl, optionally substituted pyrrolylmethyl, optionally substituted imidazolylmethyl, optionally substituted triazolylmethyl, and optionally substituted thiazolylmethyl; and more specific examples of $C_{3-8}$ cycloalkylcarbonylaminoalkyl include carbonylaminoalkyl to which cycloalkyl having 3 to 8 carbon atoms is attached.

In formulae (I) and (II), more specific examples of optionally substituted condensed heterocyclic group include optionally substituted chromanyl, optionally substituted benzoxazolyl, optionally substituted benzisoxazolyl, optionally substituted benzo[1,4]dioxanyl, optionally substituted benzothiazolyl, optionally substituted benzisothiazolyl, optionally substituted quinolyl, optionally substituted isoquinolyl, and optionally substituted indolyl. Here, preferred substituents include $C_{1-6}$ alkyl optionally substituted by a halogen atom, hydroxyl, and $C_{1-6}$ alkoxy, and methyl is more preferred. The substituents may be the same or different, and the presence of a plurality of substituents is possible. Benzo[1,4]dioxanyl is preferably unsubstituted.

In formulae (I), (II), and (III), more specific examples of optionally substituted carbamoyl include such groups that carbamoyl (H$_2$NCO—) or a nitrogen atom constituting the carbamoyl has been mono- or di-substituted, for example, by $C_{1-6}$ alkyl, $C_{3-6}$ cycloalkyl, $C_{1-6}$ hydroxyalkyl, $C_{1-6}$ dihydroxyalkyl, $C_{1-6}$ carbamoylalkylcarbamoylalkyl, $C_{1-6}$ dialkylaminoalkyl, $C_{1-6}$ cyanoalkyl, $C_{1-6}$ alkoxyalkyl, or $C_{1-6}$ halogenated alkyl; and more specific examples of optionally substituted carbamoyl $C_{1-6}$ alkyl include such groups that carbamoylmethyl ($H_2NCOCH_2-$) or a nitrogen atom constituting the carbamoylmethyl has been mono- or di-substituted, for example, by $C_{1-6}$ alkyl, $C_{3-6}$ cycloalkyl, $C_{1-6}$ hydroxyalkyl, $C_{1-6}$ dihydroxyalkyl, $C_{1-6}$ carbamoylalkylcarbamoylalkyl, $C_{1-6}$ dialkylaminoalkyl, $C_{1-6}$ cyanoalkyl, $C_{1-6}$ alkoxyalkyl, or $C_{1-6}$ halogenated alkyl; and more specific examples of optionally substituted thiocarbamoyl $C_{1-6}$ alkyl include such groups that thiocarbamoylmethyl ($H_2NCSCH_2-$) or a nitrogen atom constituting the thiocarbamoylmethyl has been substituted, for example, by $C_{1-6}$ alkyl.

In formulae (I) and (II), more specific examples of heteroarylcarbonyl include pyridylcarbonyl, pyrrolylcarbonyl, and thiazolylcarbonyl; and more specific examples of halogenated $C_{1-6}$ alkyl include $C_{1-6}$ alkyl substituted by a halogen atom, for example, chloromethyl, fluoromethyl, or fluoroethyl.

In formulae (I) and (II), more specific examples of optionally substituted heteroarylhydroxyalkyl include pyridylhydroxymethyl, thiazolylhydroxymethyl, pyrimidylhydroxymethyl, and pyrrolylhydroxymethyl.

In formulae (III) and (IV), the expression "two adjacent substituents" means that the two substituents are in such a positional relationship that carbon atoms to which the respective substituents are attached are chemically bonded to each other.

In formulae (III) and (IV), the term "five- to seven-membered ring nonaromatic hydrocarbocyclic group" refers to a nonaromatic hydrocarbocyclic group having 5 to 7 carbon atoms, and examples thereof include cyclopentyl, cyclohexyl, and cycloheptyl.

In formulae (III) and (IV), the term "five- to seven-membered ring nonaromatic heterocyclic group" refers to a nonaromatic heterocyclic group having 1 to 4 heteroatoms, and examples thereof include pyrrolidinyl, imidazolidinyl, pyrazolidinyl, piperidinyl, piperazinyl, morpholinyl, tetrahydropyranyl, dioxanyl, piperidin-2-oxoyl, dihydro-[1,3]oxazin-2-oxoyl, [1,4]oxazepan-5-oxoyl, dihydro-[1,3]oxazin-2,4-dioxoyl, 5,6-dihydro-1H-pyridin-2-oxoyl, tetrahydropyran-4-oxoyl, 2,3-dihydropyran-4-oxoyl, tetrahydropyran-4-hydroxyyl, oxepan-4-oxoyl, and 1,3-oxazolidin-2-oxoyl.

In formulae (III) and (IV), examples of "six-membered ring aromatic hydrocarbocyclic group" include phenyl.

In formulae (III) and (IV), examples of "five- or six-membered ring aromatic heterocyclic group" include (1) nitrogen-containing aromatic heterocyclic groups, for example, pyrrolyl, pyridyl, pyridazinyl, pyrimidinyl, pyrazinyl, pyrazolyl, and imidazolyl, (2) sulfur-containing aromatic heterocyclic group, for example, thienyl, (3) oxygen-containing aromatic heterocyclic groups, for example, furyl and benzofuranyl, and (4) aromatic heterocyclic groups containing two or more heteroatoms selected from the group consisting of nitrogen, sulfur, and oxygen atoms, for example, thiazolyl, isothiazolyl, oxazolyl, and isoxazolyl.

In formulae (III) and (IV), the term "$C_{2-6}$ alkenyl" refers to alkenyl having 2 to 6 carbon atoms, and preferred examples thereof include straight chain or branched chain alkenyls, for example, vinyl, allyl, 1-propenyl, isopropenyl, 1-buten-1-yl, 1-buten-2-yl, 1-buten-3-yl, 2-buten-1-yl, and 2-buten-2-yl.

In formulae (III) and (IV), the term "$C_{2-6}$ alkynyl" refers to alkynyl having 2 to 6 carbon atoms, and preferred examples thereof include straight chain or branched chain alkynyls, for example, ethynyl, 1-propynyl, 2-propynyl, butynyl, pentynyl, and hexynyl.

In formulae (III) and (IV), the term "$C_{3-8}$ cycloalkyl" refers to cyclic alkyl having 3 to 8 carbon atoms, and preferred examples thereof include cyclopropyl, cyclobutyl, cyclopentyl, cyclohexyl, cycloheptyl, and cyclooctyl.

In formulae (III) and (IV), the term "$C_{1-6}$ alkylthio" refers to such a group that one hydrogen atom in alkyl having 1 to 6 carbon atoms has been substituted by a sulfur atom, and preferred examples thereof include methylthio, ethylthio, n-propylthio, isopropylthio, n-butylthio, isobutylthio, tert-butylthio, n-pentylthio, isopentylthio, neopentylthio, n-hexylthio, and 1-methylpropylthio.

In formulae (III) and (IV), the expression "$C_{5-6}$ cycloalkyl formed by two $C_{1-3}$ alkyls attached to the same carbon atom" refers to cyclopentyl or cyclohexyl.

In formulae (III) and (IV), the expression "amino optionally substituted by $C_{1-6}$ alkyl" refers to amino to which alkyls having 1 to 6 carbon atoms have been attached, and preferred examples thereof include amino, methylamino, ethylamino, and propylamino.

In formulae (III) and (IV), the expression "amino optionally substituted by formyl" refers to, for example, amino or formylamino.

In formulae (III) and (IV), the expression "amino optionally substituted by $C_{1-6}$ alkanoyl" refers to amino to which alkanoyls having 1 to 6 carbon atoms have been attached, and preferred examples thereof include acetylamino, propionylamino, and butyrylamino.

In formulae (III) and (IV), the expression "amino optionally substituted by $C_{1-6}$ alkylsulfonyl" include amino to which alkylsulfonyls having 1 to 6 carbon atoms have been attached, and preferred examples thereof include amino, methanesulfonylamino, ethanesulfonylamino, n-propanesulfonylamino, n-butanesulfonylamino, and N-methylmethanesulfonylamino.

In formulae (III) and (IV), the expression "carbamoyl optionally substituted by 1 or 2 $C_{1-6}$ alkyls" refers to such a group that 1 or 2 hydrogen atoms in carbamoyl have been optionally mono- or di-substituted by $C_{1-6}$ alkyl, and preferred examples thereof include N-methylcarbamoyl, N,N-dimethylcarbamoyl, N-ethylcarbamoyl, and N,N-diethylcarbamoyl.

In formulae (III) and (IV), the term "$C_{1-6}$ alkoxyimino" refers to such a group that a hydrogen atom in imino has been substituted by $C_{1-6}$ alkoxy, and preferred examples thereof include methoxyimino and ethoxyimino.

In the present invention, suitable examples of compounds represented by general formulae (I), (II) and (III) include the following compounds.

Compound 1: N-methyl-{1-[1-(2-fluorophenethyl)piperidin-4-yl]-1H-indol-6-yl}acetamide

[Chemical formula 15]

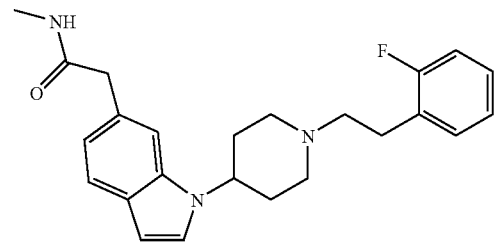

Compound 2: N-{1-[1-(2-fluorophenethyl)piperidin-4-yl]-1H-indol-6-yl}methylacetamide

[Chemical formula 16]

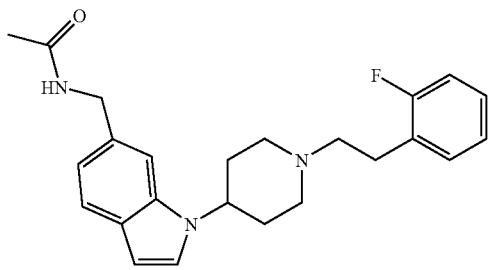

Compound 3: 1-{1-[1-(2-fluorophenethyl)piperidin-4-yl]-1H-indol-6-yl}methyl-3-methylthiourea

[Chemical formula 17]

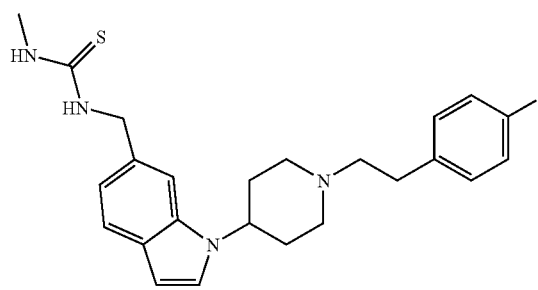

Compound 4: N-{1-[1-(2-fluorophenethyl)piperidin-4-yl]-1H-indolin-6-yl}methylacetamide

[Chemical formula 18]

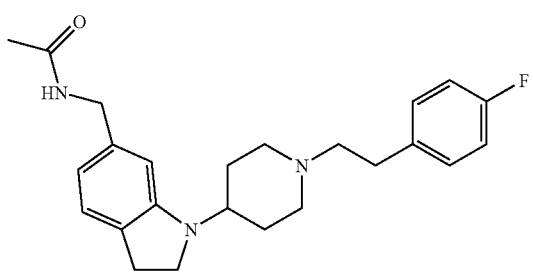

Compound 5: N-{1-[1-(4-fluorophenethyl)piperidin-4-yl]-1H-indolin-6-yl}methyl-methanesulfonamide

[Chemical formula 19]

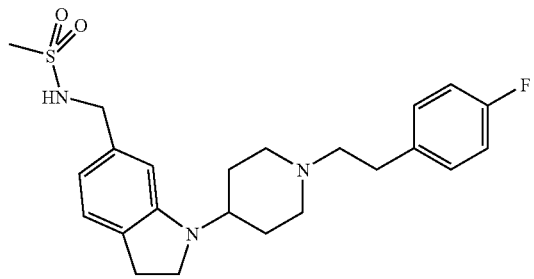

Compound 6: 1-[1-(4-fluorophenethyl)piperidin-4-yl]-6-methoxyindoline

[Chemical formula 20]

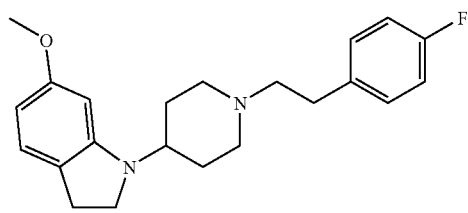

In the present invention, compounds 7 and 8 may be mentioned as the 1,4-substituted cyclic amine derivative having serotonin receptor antagonist activity.

Compound 7: 2-{4-[1-(4-ethylpiperazin-1-yl)isoquinolin-3-yl]phenoxy}ethanol

[Chemical formula 21]

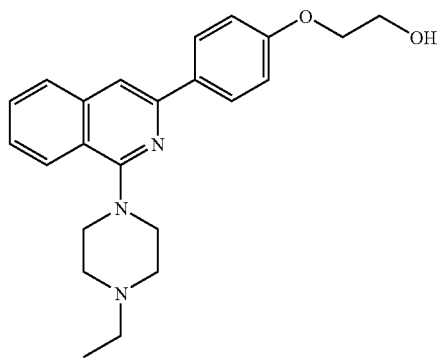

Compound 8: 1-{4-[4-(4-ethylpiperazin-1-yl)thieno[3,2-c]pyridin-6-yl]phenoxy}-2-methylpropan-2-ol

[Chemical formula 22]

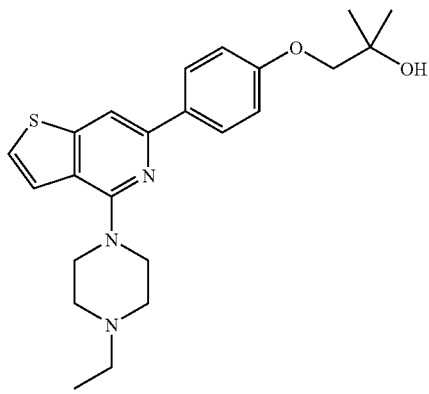

In the present invention, suitable examples of compounds represented by general formulae (I), (II), (III), and (IV) include the following compounds.

Compound 9: 1-{1-[2-(7-methoxy-2,2-dimethyl-4-oxochroman-8-yl)ethyl]piperidin-4-yl}-N-methyl-1H-indole-6-carboxamide

[Chemical formula 23]

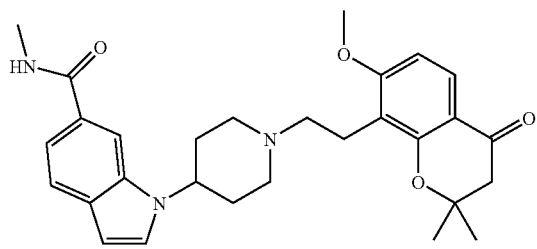

Compound 10: 1-{1-[2-(7-methoxy-2,2-dimethyl-4-oxochroman-8-yl)ethyl]piperidin-4-yl}-1H-indole-6-carboxamide

[Chemical formula 24]

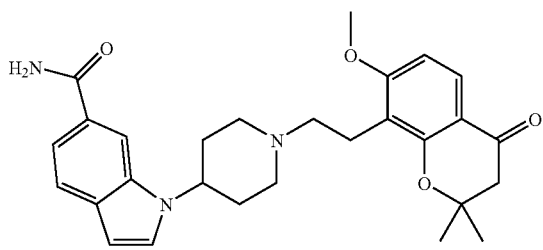

Compound 11: 1-{1-[2-(6-methoxy-2-methylbenzoxazol-5-yl)ethyl]piperidin-4-yl}-1H-indole-6-carboxamide

[Chemical formula 25]

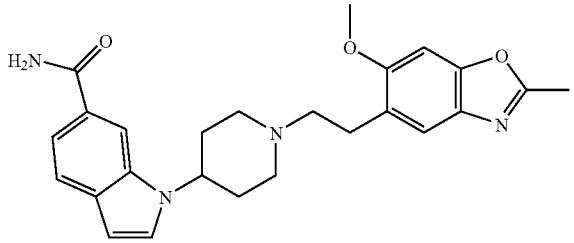

Compound 12: 1-{1-[2-(6-methoxy-2-methylbenzoxazol-7-yl)ethyl]piperidin-4-yl}-1H-indole-6-carboxamide

[Chemical formula 26]

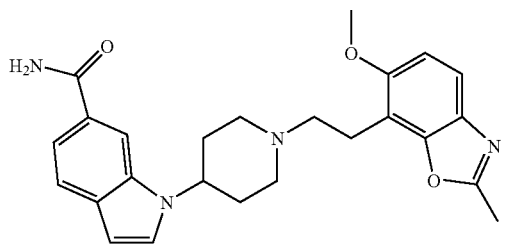

Compound 13: 1-{1-[2-(6-methoxy-3-methylbenzo[d]isoxazol-5-yl)ethyl]piperidin-4-yl}-1H-indole-6-carboxamide

[Chemical formula 27]

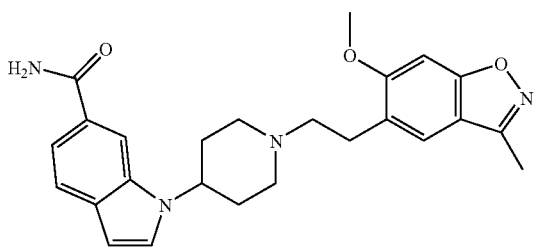

Compound 14: 1-{1-[2-(6-methoxy-3-methylbenzo[d]isoxazol-7-yl)ethyl]piperidin-4-yl}-1H-indole-6-carboxamide

[Chemical formula 28]

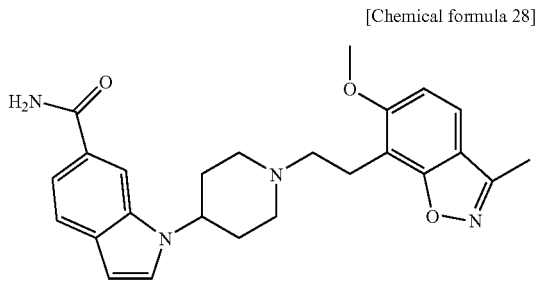

Compound 15: 1-{1-[2-(7-methoxy-2,3-dihydrobenzo[1,4]dioxin-6-yl)ethyl]piperidin-4-yl}-1H-indole-6-carboxamide

[Chemical formula 29]

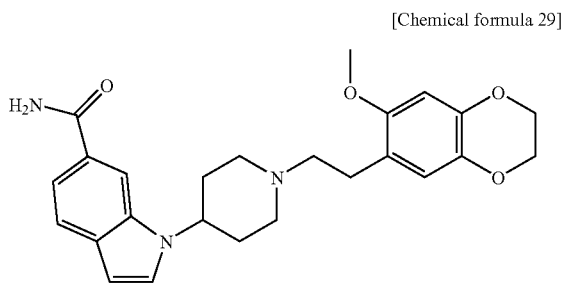

For compounds 1 to 6, regarding the results of a serotonin 1A receptor binding test and a serotonin 2 receptor binding test, reference may be made to a pamphlet of International Publication No. 98/43956. The results will be described later as Reference Example.

Further, for compounds 7 and 8, regarding the results of a serotonin 1A receptor binding test and a serotonin 2 receptor binding test, reference may be made to a pamphlet of International Publication No. 99/18077. The results will be described later as Reference Example.

For compounds 9 to 15, regarding the results of a serotonin 1A receptor binding test, reference may be made to a pamphlet of International Publication No. 2005/108389. The results will be described later as Reference Example.

Compounds having anticoagulant activity and antidepressant activity are also known to have 5HT2A receptor antagonist activity, and, thus, anticoagulants and antidepressants are also usable as therapeutic agents for motor neuron diseases. Specifically, anticoagulants include, for example, sarpogrelate, and antidepressants include, for example, trazodone, nortriptyne, amitriptine, imipramine, paroxetine, fluvoxamine, milnacipran, mirtazapine, mianserin, MDL-11939, and MDL100907.

Some therapeutic agents for schizophrenia are also known to have 5HT2A receptor antagonist activity, and, thus, these therapeutic agents for schizophrenia are also usable as therapeutic agents for motor neuron diseases. Specific examples of therapeutic agents for schizophrenia include, for example, olanzapine, risperidone, perospirone, quetiapine, clocapramine, carpipramine, mosapramine, chlorpromazine, and levomepromazine.

In the present invention, for convenience, the structural formula of a compound sometimes represents a given isomer. However, it should be noted that all of isomers provided in the structure of the compounds, such as geometrical isomers, optical isomers based on asymmetric carbon, rotational isomers, stereoisomers, and tautomers and isomeric mixtures composed of two or more of the above isomers fall within the scope of the present invention. Accordingly, the present invention is not limited to the description of the formula of convenience, and any one of the isomers or a mixture of these isomers is possible. Therefore, it is likely that, in the present invention, the above "compound having serotonin receptor antagonist activity" has an asymmetric carbon atom in its molecule and an optically active substance and racemete exist. However, the present invention is not limited to this, and all the cases are embraced in the present invention. Further, in some cases, a crystal polymorphism exists. This case, however, does not also limit the present invention, and a single crystal form or a mixture of crystal form is possible.

In the present invention, the "compound having serotonin receptor antagonist activity" or its pharmacologically acceptable salt may be in an anhydride or hydrate form. These anhydrides and hydrates fall within the scope of the compound having serotonin receptor antagonist activity in the present invention. Further, in the present invention, the "compound having serotonin receptor antagonist activity" or its pharmacologically acceptable salt may be in a solvate form. These solvates also fall within the scope of the compound having serotonin receptor antagonist activity. The solvate may be in a hydrate or nonhydrate form. Among others, the hydrate form is preferred. Nonhydrates usable herein include, for example, alcohols, for example, methanol, ethanol, and n-propanol, and N,N-dimethylformamide.

In the present invention, the compound having serotonin receptor antagonist activity embraces the above "compound having serotonin receptor antagonist activity," which undergoes metabolism in vivo such as oxidation, reduction, hydrolysis and conjugation, as well as metabolites produced as a result of metabolism in vivo. Further, in the present invention, the compound having serotonin receptor antagonist activity also embraces compounds (prodrugs) that undergo metabolism in vivo such as oxidation, reduction, hydrolysis and conjugation to produce the "compound having serotonin receptor antagonist activity" (including its pharmacologically acceptable salt or solvate).

In the present invention, the "pharmacologically acceptable salt" is not particularly limited so far as it, together with the "compound having serotonin receptor antagonist activity," forms a salt and is pharmacologically acceptable. Preferred salts include, for example, halogenated hydroacid salts, for example, hydrochloride, hydrobromate, and hydroiodide; inorganic acid salts, for example, sulfate, nitrate, perchlorate, phosphate, carbonate, and bicarbonate; organic carboxylates, for example, acetate, trifluoroacetate, maleate, tartrate, fumarate, and citrate; organic sulfonates, for example, methanesulfonate, trifluoromethanesulfonate, ethanesulfonate, benzenesulfonate, toluenesulfonate, and camphorsulfonate; amino acid salts, for example, aspartate and glutamate; quaternary amine salts; alkali metal salts, for example, sodium salt and potassium salt; and alkali-earth metal salts, for example, magnesium salt and calcium salt.

In the present invention, the term "prodrug" means an agent that comprises "active drug" (meaning "drug" corresponding to prodrug) which has been chemically modified into an inert substance, for example, from the viewpoints of improving bioavailability and reducing side effects, and, upon absorption, is metabolized in vivo into an active drug which develops the activity. Accordingly, the term "prodrug" refers to any compound that has lower intrinsic activity than the corresponding "drug" but, upon administration to a biological system, produces the "drug" substance as a result of a spontaneous chemical reaction or an enzyme catalyzed reaction or a metabolic reaction. Examples of such prodrugs include various prodrugs, for example, compounds produced by acylation, alkylation, phosphorylation, boration, carbonation, esterification, amidation, or urethanation of an amino, hydroxyl, carboxyl or other group in the "compound having serotonin receptor antagonist activity." However, it should be noted that the exemplified prodrugs are not comprehensive and are merely typical, and other conventional various prodrugs can be prepared by a conventional method by a person having ordinary skill in the art from the "compound having serotonin receptor antagonist activity" (including its pharmacologically acceptable salt or solvate). Prodrugs comprising the "compound having serotonin receptor antagonist activity" fall within the scope of the present invention.

In the present invention, the "compound having serotonin receptor antagonist activity" or its pharmacologically acceptable salt or their solvate or their prodrug (often abbreviated, in the present specification, also to "compound having serotonin receptor antagonist activity") can be obtained by conventional production processes when it is a known compound, or by a conventional extraction method or a conventional purification method when it is a naturally occurring compound, or by the purchase of a commercially available product. For example, derivatives of known compounds can be modified by chemical means, physical means and/or biochemical means.

In the present invention, the 1,4-substituted cyclic amine derivative or its pharmacologically acceptable salt or their solvate or their prodrug may be produced by a conventional process. The 1,4-substituted cyclic amine derivative or its pharmacologically acceptable salt or their solvate can easily be produced typically, for example, by a process disclosed, for example, in a pamphlet of International Publication No. 98/43956, U.S. Pat. No. 6,340,759, or a pamphlet of International Publication No. 2005/108389 or a technique based on the process.

In the present invention, compounds represented by general formula (I), (II), and (III), more specifically compounds 1 to 6, may be produced by a conventional process. They can easily be produced typically by a process disclosed in a pamphlet of International Publication No. 98/43956 or a technique based on the process.

Compound 1: N-Methyl-{1-[1-(2-fluorophenethyl)piperidin-4-yl]-1H-indol-6-yl}acetamide can easily be produced by a process disclosed in Example 342 in a pamphlet of International Publication No. 98/43956 or a technique based on the process.

Compound 2: N-{1-[1-(2-Fluorophenethyl)piperidin-4-yl]-1H-indol-6-yl}methylacetamide can easily be produced by a process disclosed in Example 352 in a pamphlet of International Publication No. 98/43956 or a technique based on the process.

Compound 3: 1-{1-[1-(2-Fluorophenethyl)piperidin-4-yl]-1H-indol-6-yl}methyl-3-methylthiourea can easily be produced by a process disclosed in Example 394 in a pamphlet of International Publication No. 98/43956 or a technique based on the process.

Compound 4: N-{1-[1-(2-Fluorophenethyl)piperidin-4-yl]-1H-indolin-6-yl}methylacetamide can easily be produced by a process disclosed in Example 133 in a pamphlet of International Publication No. 98/43956 or a technique based on the process.

Compound 5: N-{1-[1-(4-Fluorophenethyl)piperidin-4-yl]-1H-indolin-6-yl}methyl-methanesulfonamide can easily be produced by a process disclosed in Example 160 in a pamphlet of International Publication No. 98/43956 or a technique based on the process.

Compound 6: 1-[1-(4-Fluorophenethyl)piperidin-4-yl]-6-methoxyindoline can easily be produced by a process disclosed in Example 106 in a pamphlet of International Publication No. 98/43956 or a technique based on the process.

Compounds 7 and 8 can be produced by a conventional process. Specifically, these compounds can easily be produced typically by a process disclosed in U.S. Pat. No. 6,340,759 or a technique based on the process.

Compound 7: 2-{4-[1-(4-Ethylpiperazin-1-yl)isoquinolin-3-yl]phenoxy}ethanol can easily be produced by a process disclosed in Example 36 in U.S. Pat. No. 6,340,759 or a technique based on the process.

Compound 8: 1-{4-[4-(4-Ethylpiperazin-1-yl)thieno[3,2-c]pyridin-6-yl]phenoxy}-2-methylpropan-2-ol can easily be produced by a process disclosed in Example 290 in U.S. Pat. No. 6,340,759 or a technique based on the process.

In the present invention, compounds represented by general formula (I), (II), (III), and (IV), more specifically compounds 9 to 15, can be produced by a conventional process. They can easily be produced typically by a process disclosed in a pamphlet of International Publication No. 2005/108389 or a technique based on the process.

Compound 9: 1-{1-[2-(7-Methoxy-2,2-dimethyl-4-oxochroman-8-yl)ethyl]piperidin-4-yl}-N-methyl-1H-indole-6-carboxamide can easily be produced by a process disclosed in Example 20 in a pamphlet of International Publication No. 2005/108389 or a technique based on the process.

Compound 10: 1-{1-[2-(7-Methoxy-2,2-dimethyl-4-oxochroman-8-yl)ethyl]piperidin-4-yl}-1H-indole-6-carboxamide can easily be produced by a process disclosed in Example 22 in a pamphlet of International Publication No. 2005/108389 or a technique based on the process.

Compound 11: 1-{1-[2-(6-Methoxy-2-methylbenzoxazol-5-yl)ethyl]piperidin-4-yl}-1H-indole-6-carboxamide can easily be produced by a process disclosed in Example 4 in a pamphlet of International Publication No. 2005/108389 or a technique based on the process.

Compound 12: 1-{1-[2-(6-Methoxy-2-methylbenzoxazol-7-yl)ethyl]piperidin-4-yl}-1H-indole-6-carboxamide can easily be produced by a process disclosed in Example 3 in a pamphlet of International Publication No. 2005/108389 or a technique based on the process.

Compound 13: 1-{1-[2-(6-Methoxy-3-methylbenzo[d]isoxazol-5-yl)ethyl]piperidin-4-yl}-1H-indole-6-carboxamide can easily be produced by a process disclosed in Example 2 in a pamphlet of International Publication No. 2005/108389 or a technique based on the process.

Compound 14: 1-{1-[2-(6-Methoxy-3-methylbenzo[d]isoxazol-7-yl)ethyl]piperidin-4-yl}-1H-indole-6-carboxamide can easily be produced by a process disclosed in Example 1 in a pamphlet of International Publication No. 2005/108389 or a technique based on the process.

Compound 15: 1-{1-[2-(7-Methoxy-2,3-dihydrobenzo[1,4]dioxin-6-yl)ethyl]piperidin-4-yl}-1H-indole-6-carboxamide can easily be produced by a process disclosed in Example 31 in a pamphlet of International Publication No. 2005/108389 or a technique based on the process.

Pharmaceutical Composition/medical Use

As demonstrated in Examples which will be described later, compounds having serotonin receptor antagonist activity could inhibit hyperexcitation of motor neuron cells. The hyperexcitation of motor neuron cells is related to motor neuron diseases, particularly ALS (Damiano M, et al., J. Neurochem., 96(5), 1349-1361, 2006, Sharifullina E, et al., J. Physiol., 15; 572(Pt 2), 407-423, 2006., and Tortarolo M, et al., J. Neurosci. Res., 83(1), 134-146, 2006.). Accordingly, compounds having serotonin receptor antagonist activity can be used for the treatment of motor neuron diseases, particularly ALS.

The pharmaceutical composition according to the present invention comprises a compound having serotonin receptor antagonist activity or its pharmacologically acceptable salt or their solvate or their prodrug as an active ingredient.

The compound having serotonin receptor antagonist activity as an active ingredient of the pharmaceutical composition according to the present invention can be administered by any proper administration route without particular limitation, for example, by oral or parenteral administration, for example, intravenous administration, intramuscular administration, subcutaneous administration, rectal administration, or percutaneous administration. Among others, the oral administration is preferred because patient burden is lower than that in enteroclysis and the like.

The dosage form for oral administration and parenteral administration and the production process thereof are well known to a person having ordinary skill in the art, and the dosage form for oral administration and parenteral administration can be produced by a conventional process, for example, by mixing the compound having serotonin receptor antagonist activity, for example, with a pharmaceutically acceptable carrier.

Dosage forms for oral administration include solid or liquid dosage forms, specifically tablets, coated tablets, pills, fine subtilaes, granules, powders, capsules, syrups, emulsions, suspensions, injections, and troches.

Dosage forms for parenteral administration include injections (including drops), external preparations (for example, ointments, poultices, or lotions), suppository inhalants, eye drops, ophthalmic ointments, nasal drops, ear drops, and liposome preparations.

The pharmaceutically acceptable carrier is, for example, a substance that is commonly used in the field of pharmaceutical preparations and is not reacted with the compound having serotonin receptor antagonist activity. Pharmaceutically acceptable carriers include, for example, commonly used excipients, binders, disintegrators, lubricants, coloring matters, corrigents, and optionally stabilizers, emulsifiers, absorbefacients, surfactants, pH adjustors, antiseptics, antioxidants, extenders, wetting agents, surface active agents, dispersants, buffers, preservatives, solubilizers, and soothing agents, and may be formulated according to a conventional method by mixing ingredients commonly used as raw materials for pharmaceutical preparations.

Excipients include, for example, lactose, fructose, corn starch, saccharose, glucose, mannitol, sorbitol, crystalline cellulose, silicon dioxide, and calcium sulfate. Binders include, for example, polyvinyl alcohol, polyvinyl ether, methylcellulose, ethylcellulose, acacia, tragacanth, gelatin, shellac, hydroxypropylmethylcellulose, hydroxypropylcellulose, polyvinylpyrrolidone, polypropylene glycol/polyoxyethylene block polymers and meglumine. Disintegrators include, for example, starch, agar, gelatin powder, crystalline cellulose, calcium carbonate, sodium hydrogencarbonate, calcium citrate, dextrin, pectin, calcium carboxymethylcellulose, carmellose sodium, and carmellose calcium. Lubricants include, for example, magnesium stearate, talc, polyethylene glycol, silica and hardened vegetable oils. Coloring matters include, for example, those authorized as pharmaceutical additives. Corrigents include, for example, cocoa powder, mentha, aromatic powder, mentha oil, borneol and powdered cinnamon bark. These ingredients may be pharmaceutically acceptable salts or their hydrates.

Additional nontoxic ingredients usable as the pharmaceutically acceptable carrier include: animal and vegetable oils, for example, soybean oils, tallows, or synthetic glycerides; hydrocarbons such as liquid paraffin, squalane, or solid paraffin; ester oils, for example, octyldodecyl myristate or isopropyl myristate; higher alcohols, for example, cetostearyl alcohol or behenyl alcohol; silicone resins; silicone oils; surfactants, for example, polyoxyethylene fatty acid esters, sorbitan fatty acid esters, glycerin fatty acid esters, polyoxyethylene sorbitan fatty acid esters, polyoxyethylene hydrogenated castor oils, or a polyoxyethylene-polyoxypropylene block copolymers; water soluble polymers, for example, hydroxyethylcellulose, polyacrylic acid, carboxyvinyl polymers, polyethylene glycol, polyvinylpyrrolidone, or methylcellulose; $C_{1-6}$ alcohols, for example, ethanol or isopropanol; polyvalent alcohols (polyols), for example, glycerin, propylene glycol, dipropylene glycol, sorbitol, or polyethylene glycol; sugars, for example, glucose or sucrose; inorganic powders, for example, silicic acid anhydride, magnesium aluminum silicate, or aluminum silicate; inorganic salts, for example, sodium chloride or sodium phosphate; and purified water.

In the formulation of oral preparations, for example, the compound having serotonin receptor antagonist activity is mixed, for example, with an excipient, for example, lactose, saccharose, starch, or mannitol, a binder, for example, pregelatinized starch, acacia, carboxymethylcellulose, or polyvinylpyrrolidone, a lubricant, for example, magnesium stearate or talc, a coloring matter, a corrigent, and a disintegrator. Thereafter, if necessary, a stabilizer, an emulsifier, an absorbefacient, a surfactant and the like are added. Thereafter, the resultant mixture may be formulated by a conventional method into tablets, powders, fine subtilaes, granules, coated tablets, capsules and the like. The tablets may be coated with a coating agent such as carnauba wax, hydroxypropylmethylcellulose, macrogol, hydroxypropylmethyl phthalate, cellulose acetate phthalate, saccharose, titanium oxide, sorbitan fatty acid ester, or calcium phosphate by a well known method.

Specific examples of carriers usable in the production of syrups include sweetening agents such as saccharose, glucose or fructose, suspending agents such as acacia, tragacanth, carmellose sodium, methylcellulose, sodium alginate, crystalline cellulose and veegum, and dispersants such as sorbitan fatty acid esters, sodium laurylsulfate, and Polysorbate 80. In the production of syrups, if necessary, for example, corrigents, aromatics, preservatives, solubilizers, stabilizers and the like may be added. The syrup may be in a dry syrup form which is dissolved or suspended before use.

Specific examples of bases for suppositories include suitable nonirritating excipients, which are solid at room temperature but are liquid at body temperature, for example, cacao butters, saturated fatty acid glycerin esters, polyethylene glycol, glycerogelatin, and macrogol. In the production of suppositories, if necessary, for example, surfactants and preservatives may be added.

Injections are generally prepared, for example, by dissolving a pharmacologically acceptable salt of the compound having serotonin receptor antagonist activity in distilled water for injections. If necessary, for example, solubilizers, buffers, pH adjustors, tonicity adjusting agents, soothing agents, preservatives, and stabilizers may be added.

Materials for bases usable in the production of external preparations include various materials commonly used, for example, in drugs, quasi drugs, and cosmetics, for example, animal and vegetable oils, mineral oils, ester oils, waxes, higher alcohols, fatty acids, silicone oils, surfactants, phospholipids, alcohols, polyhydric alcohols, water soluble polymers, clay minerals, and purified water. If necessary, for example, pH adjustors, antioxidants, chelating agents, antiseptics and fungicides, coloring matters, and perfumes may also be added.

In the case of inhalants, for administration through inhalation, the compound having serotonin receptor antagonist activity can be delivered through an insufflator, a sprayer, or a pressure pack or other convenient manner which can deliver aerosol spray. The pressure pack can comprises a suitable propellant. For the administration through inhalation, the compound having serotonin receptor antagonist activity can also be administered in the form of a dry powder composition or liquid spray.

For topical administration to the skin, the compound having serotonin receptor antagonist activity can be formulated as ointments, creams, or lotions or as an active ingredient for "percutaneous patches." The ointments and creams can be formulated, for example, by adding a suitable thickening agent and/or a gelatinizing agent to a water-based or oil-based base. The lotions can be formulated by using a water-based or oil-based base. Further, in general, these preparations can also contain one type or a plurality of types of emulsifiers, stabilizers, dispersants, suspending agents, thickening agents and/or coloring matters.

The pharmaceutical composition according to the present invention may further contain therapeutically effective other medicaments. Further, if necessary, for example, blood flow accelerating agents, disinfectants, antiphlogistic agents, cell activating agents, vitamins, amino acids, humectants, and keratolytic agents may also be added. In this case, the ratio of the effective ingredient to the carrier may vary in the range of 1 to 90% by weight.

These pharmaceutical compositions may generally contain, as an active ingredient, not less than 0.5% (% by weight; the same shall apply hereinafter), preferably 10 to 70%, of the compound having serotonin receptor antagonist activity. When the compound having serotonin receptor antagonist activity is used for the above treatment, preferably, the compound has been purified to a level of not less than 90%, preferably not less than 95%, more preferably not less than 98%, still more preferably not less than 99%.

The dose of the compound having serotonin receptor antagonist activity may be determined by clinicians, for example, in consideration of various factors, for example, administration route, type of disease, severity of condition, the age, sex, and weight of patients, type of salt, specific type of diseases, pharmacological finding such as pharmacokinetics and toxicologic features, whether or not a drug delivery system is utilized, and whether or not the compound having serotonin receptor antagonist activity is used as a part of a combination with other medicament(s), and may be generally about 30 µg to 10 g/day, preferably 100 µg to 5 g/day, still preferably 100 µg to 100 mg/day, for oral administration, and about 30 µg to 1 g/day, preferably 100 µg to 500 mg/day, still preferably 100 µg to 30 mg/day, for injection administration, each per adult (weight 60 kg). This dose may be administered at a time daily or divided doses of several times. When administration to children is contemplated, the dose is possibly smaller than the dose for administration to adults. The actually adopted dosage regimen is sometimes significantly varied by judgment of clinicians and is sometimes deviated from the above-defined dose range.

In the present invention, the "motor neuron disease (motor neuron degeneration disease)" is classified, based on the diagnostic criteria of "International Statistical Classification of Disease and Related Health Problems, 10th edition (ICD-10)," established by World Health Organization (WHO), in "G12: spinal muscular atrophy and related syndromes" in chapter VI (G) "Diseases of the nervous system" and is preferably classified in "G12.2: motor neuron disease." Specific examples of motor neuron diseases include Werdnig-Hoffmann diseases, distal spinal muscular atrophy, familial spinal muscular atrophy, scapular fibular spinal muscular atrophy, juvenile progressive muscular atrophy, infantile progressive muscular atrophy, infant progressive bulbar palsy, diffuse atrophic paralysis, motor neuron diseases, pseudobulbar palsy, familiar amyotrophic lateral sclerosis, bulbar palsy, amyotrophic lateral sclerosis, juvenile unilateral upper-limb muscular atrophy, progressive bulbar palsy, progressive muscular dystrophy, spinal progressive muscular atrophy, traumatic bulbar palsy, spinobulbar muscular atrophy, cervical spondylotic muscular atrophy, and spinal muscular atrophy.

The term "treatment" as used herein generally means attaining desired pharmacological effect and/or physiological effect. This effect is prophylactic in that a disease and/or a symptom are completely or partially prevented, and is therapeutic in that a disease and/or adverse effect attributable to a disease are partially or completely cured. The term "treatment" as used herein embraces any treatment of diseases of patients, particularly humans, for example:

prevention of the occurrence of a disease or symptom in a patient who may have predisposition to the disease or symptom but is not yet diagnosed as having the disease or symptom;

inhibition of the symptom of a disease, that is, preventing or delaying the progress;

alleviation of the symptom of a disease, that is, inducing regression or disappearance of a disease or a symptom, or reversion of the progress of a symptom.

For example, clinical symptoms of motor neuron diseases include: amyotrophy and muscle weakness, for example, amyotrophy of upper limb distal part, bulbar palsy, and amyotrophy of lower limb; respiratory muscle paralysis, for example, dyspnea; bulbar palsy, for example, dysphagia and hypophonia; negative signs, for example, vesicorectal disorders, eye movement disorders, and sensory disorders; pyramidal tract symptoms, for example, dysbasia; and muscular fasciculation.

The expression "prevention of the progress of motor neuron diseases" is interpreted as meaning the prevention of the onset of clinical symptoms and/or pathological signs of a motor neuron disease or the prevention of the progress of the clinical symptoms and/or pathological signs. For example, in a patient, who does not have a clinical symptom or pathological sign of a motor neuron disease, the progress of the clinical symptom or pathological sign can be prevented. Further, in a patient, who suffers from a mild motor neuron disease, the onset of the form of a severer motor neuron disease can be prevented. The expression "delaying the progress of motor neuron diseases" is interpreted as meaning delaying the time of the onset of motor neuron disease-related symptom and/or pathological sign, or delaying the progression rate of the motor neuron disease determined by the progression rate of the clinical symptom and pathological sign. The expression "reversion of the progress of the motor neuron diseases" is interpreted as meaning alleviation of the severity of the motor neuron disease symptom, that is, a change in the motor neuron disease symptom of a patient from severe to mild state. In this case, the change to milder state is indicated by a reduction in clinical symptom or pathological sign.

The motor neuron disease of a patient can be diagnosed by conventional various methods.

Typically, the motor neuron disease can be diagnosed by using a combination of clinical evaluation with pathological evaluation.

The term "patient" as used herein refers to animals, preferably mammals. In this case, the term "mammal" embraces all of animals classified as mammals, for example, human or nonhuman mammals, for example, mice, rats, hamsters, guinea pigs, rabbits, swines, dogs, horses, cattles, and monkeys. Preferably, in the present specification, the mammal is human. In this case, the term "patient" embraces adults and children, and embraces male and female. The children includes newborns, infants, and young people.

EXAMPLES

Example 1

Evaluation on Toxicity of 5HT in Rat Motor Neuron Primary Pure Culture System

1. Experimental Conditions and Experimental Method

Rat motor neuron cells were subjected to pure culture in the presence of 30 ng/mL BDNF for three days, and toxicity of serotonin (5HT) was evaluated.

1. Rat Motor Neuron Primary Pure Culture

The rat motor neuron primary pure culture was carried out by a method which is modification of Nishijima et al. method (Nishijima C. et al., J Neurochem 76, 383-390(2001)) by incorporating a purification method and the like in the Nishijima et al. method.

A necessary number of Greiner-4-well dishes (10 mm i.d. wells) (Greiner bio-one) were provided, and 0.15 M sodium borate buffer (pH 8.3) containing 0.5 mg/mL poly-L-ornithine was added at 100 µL/well followed by standing at 4° C. overnight. Ornithine was removed by suction, the residue was washed three times with PBS(−), and L-15 ($CO_2$) containing 10 µg/mL laminin (Gibco-BRL) was spread at 50 µL/well. Until cell seeding, the Greiner-4-well dishes were stored in a $CO_2$ incubator (5%, 37° C.).

Wistar pregnant rats (fifteen days pregnant) (Tokyo Laboratory Animals Science Co., Ltd.) were etherized and were then sacrificed by cervical dislocation. A fetus was removed aseptically from the uterus in each rats and was transferred to a cold HBSS(−)-containing 100 mm-dish (HBSS(−): HBSS (−) (GIBCO-BRL, Catalog No. 14170)). A lumbar spinal cord (length: about 5 mm) was removed under a stereomicroscope. Further, a spinal ventral part was excised in the purest possible state and was stored in cold HBSS(−). Likewise, the spinal ventral part in 6 to 10 rats was removed and, transferred to a 50-mL tube, and was lightly washed with cold HBSS(−), and 2 mL of HBSS(−) containing 0.03% trypsin was added thereto, followed by incubation while light shaking at 37° C. for 20 min. After light washing with cold HBSS(−), the spinal ventral part was then transferred to a 15-mL tube containing 1 mL of HBSS(−) containing 0.2% BSA. Pipetting was repeated mildly 10 times with a silicone-treated Pasteur pipette with a rounded tip to disintegrate the tissue. The supernatant was sieved through 70-µm mesh, and cell measurement was carried out with a counting plate. Until the cells could be fully recovered, the procedure consisting of adding 1 mL of 0.2% BSA-containing HBSS(−) and disintegrating the tissue was repeated four times in total. The recovered cell suspension was placed in a 12 mL-siliconized glass tube containing 4 mL of 6.5% iopamiron-containing HBSS(−), and the mixture was centrifuged (400×g, 4° C., 15 min). The cells at the interface were recovered with a 100 µL Pipetman (5 times in total). The recovered cells were added to a 15-mL tube containing 5 mL of the culture solution, and the mixture was lightly stirred and was centrifuged (100×g, 4° C., 8 min). The supernatant was discarded as completely as possible, 1 mL of the culture solution was added, the cells were refloated, and cell measurement was conducted with a counting plate. Based on the measurement results, the cells were diluted to 1.1 to $1.2 \times 10^4$ cell/mL with the culture solution. Greiner 4-well dishes previously coated with poly-L-ornithine (Sigma)/laminin (Gibco-BRL) were seeded with the cell suspension at 90 µL/well with 1-mL Pipetman. One hr after the start of the culture, serotonin (serotonin creatinine sulfate complex, Sigma) or glutamate (Sigma) was added thereto, and, three hr after that, the initial viable cell count was measured. The viable cell count was again measured three days after the cell seeding, and the survival rate was calculated based on the initial viable cell count. The cell count measurement was carried out under a phase-contrast microscope using marks previously applied on the backside of the Greiner 4-well dish as a reference. Only cells, which had a large cell body (not less than about 15 µmϕ) and were phase bright, were measured.

A culture solution (L-15($CO_2$)-10% HS) prepared by mixing 15 mL of 0.15 M sodium bicarbonate, 75 mL of a Leibovitz's L-15 culture solution (GIBCO), and glucose together, adjusting the pH value of the mixture with $CO_2$ to give a solution (hereinafter referred to also as "L-15 ($CO_2$)"), and adding 10%-heat-inactivated horse serum (HS), 100 units/mL penicillin G, and 30 ng/mL human BDNF (peprotech, Inc.) to L-15 ($CO_2$) was used as a standard culture solution. A culture solution comprising supplement (B27 (0.2 mL) or N-2 (0.1 mL)) and 100 units/mL penicillin G added to 10 mL of Neurobasal™ (Gibco-BRL) was used as a serum-free culture solution.

2. Experimental Results

Figure 1B:
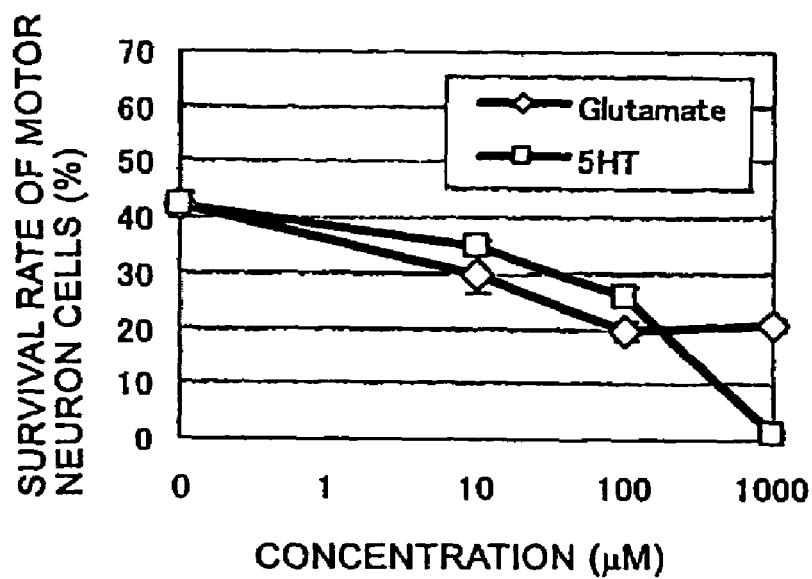

The results are shown in FIG. 1. 5HT showed toxicity in a concentration-dependent manner (FIG. 1A), and this toxicity was comparable with glutamate toxicity (FIG. 1B). About 10 µM glutamate was detected in a standard culture solution containing 10% horse serum. Accordingly, a serum-free culture solution not containing glutamate was used for evaluation by comparison with glutamate toxicity although, in this case, the survival rate was lowered.

Example 2

Analysis of Receptor Involved in 5HT Toxicity in Rat Motor Neuron Primary Pure Culture System Regarding the participation of each receptor in 5HT toxicity, the present inventor has paid attention to 5HT1A and 5HT2A receptors, which are main receptors of 5HT in the rat fetal phase, and the participation of these receptors in 5HT toxicity was evaluated using each antagonist.

1. Experimental Conditions and Experimental Method

Rat motor neuron primary pure culture was carried out in the same manner as in Example 1 to prepare rat motor neuron cells. Based on the results of cell measurement, the rat motor neuron cells were diluted with the culture solution to 1.1 to $1.2 \times 10^4$ cells/mL. Greiner 4-well dishes previously coated with poly-L-ornithine/laminin were seeded with the cell suspension at 90 μL/well with a 1 mL Pipetman. One hr after the start of culture, a 5HT1A receptor antagonist NAN-190 (TOCRIS) or a 5HT2A receptor antagonist MDL-11939 (TOCRIS) was added, and serotonin (5HT) was added thereto 5 to 10 min after the addition of the antagonist. The initial viable cell count was measured three hr after the addition of serotonin (5HT). The viable cell count was again measured three days after the cell seeding, and the survival rate was calculated based on the initial viable cell count. The cell count measurement was carried out under a phase-contrast microscope using marks previously applied on the backside of the Greiner 4-well dish as a reference. Only cells, which had a large cell body (not less than about 15 μmϕ) and were phase bright, were measured.

2. Experimental Results

The results are shown in FIG. 2. The 5HT toxicity was inhibited by the 5HT1A receptor antagonist NAN-190 and 5HT2A receptor antagonist MDL-11939 (FIG. 2A and FIG. 2B). The results demonstrate that the two receptors, 5HT1A and 5HT2A, are involved in 5HT toxicity. The evaluation of the survival activity using the culture system was analyzed by using analysis of variance and Dunnett test/Bonferoni test.

Example 3

Analysis of IP3 Receptor Involved in 5HT Toxicity in Rat Motor Neuron Primary Pure Culture System Since IP3 receptors on endoplasmic reticula as a downstream element of signals through 5HT2A receptors had been estimated to be involved in 5HT toxicity, studies have been made on the inhibition of 5HT excitotoxicity by 2-APB, i.e., an IP3 receptor antagonist.

1. Experimental Conditions and Experimental Method

Rat motor neuron primary pure culture was carried out in the same manner as in Example 1 to prepare rat motor neuron cells. Based on the results of cell measurement, the rat motor neuron cells were diluted with the culture solution to 1.1 to $1.2 \times 10^4$ cells/mL. Greiner 4-well dishes previously coated with poly-L-ornithine/laminin were seeded with the cell suspension at 90 μL/well with a 1 mL Pipetman. One hr after the start of culture, an IP3 receptor antagonist 2-APB (TOCRIS), a 5HT2C receptor agonist MK-212 (TOCRIS), an $\alpha 1$ receptor agonist phenylephrine (Sigma), an $\alpha 2$ receptor agonist clonidine (WAKO), a nicotinic Ach receptor agonist nicotine (Sigma), or a muscarinic Ach receptor agonist pilocarpine (Sigma) was added, and serotonin (5HT) was added thereto 5 to 10 min after the addition of the antagonist or agonist. The initial viable cell count was measured three hr after the addition of serotonin (5HT). The viable cell count was again measured three days after the cell seeding, and the survival rate was calculated based on the initial viable cell count. The cell count measurement was carried out under a phase-contrast microscope using marks previously applied on the backside of the Greiner 4-well dish as a reference. Only cells, which had a large cell body (not less than about 15 μmϕ) and were phase bright, were measured.

2. Experimental Results

The results are shown in FIGS. 3 and 4. The inhibition of 5HT excitotoxicity by 2-APB as an IP3 receptor antagonist could be confirmed by the above studies (FIG. 3). This fact also demonstrates the participation of 5HT2A receptor in excitotoxicity. Agonists of various other receptors (5HT2C receptors, $\alpha 1$ receptors, $\alpha 2$ receptors, nicotinic Ach receptors, and muscarinic Ach receptors) known to be expressed in motor neuron cells had no significant effect on the survival rate (FIG. 4).

The evaluation of the survival activity using the culture system was analyzed by using analysis of variance and Dunnett test/Bonferoni test.

Example 4

Evaluation of Antidepressant Trazodone having 5HT2A Receptor Antagonist Activity in Rat Motor Neuron Primary Pure Culture System It was found that 5HT has excitotoxicity against cultured motor neuron cells and 5HT1A and 5HT2A receptors are involved in the action of 5HT on the motor neuron cells. In particular, it was suggested that 5HT2A receptors are specifically expressed in motor neuron cells in the spinal cord and the 5HT toxicity through 5HT2A receptors is involved in the progress of ALS. Accordingly, evaluation was made on clinically applicable 5HT2A receptor antagonists.

1. Experimental Conditions and Experimental Method

Rat motor neuron primary pure culture was carried out in the same manner as in Example 1 to prepare rat motor neuron cells. Based on the results of cell measurement, the rat motor neuron cells were diluted with the culture solution to 1.1 to $1.2 \times 10^4$ cells/mL. Greiner 4-well dishes previously coated with poly-L-ornithine/laminin were seeded with the cell suspension at 90 μL/well with a 1 mL Pipetman. One hr after the start of culture, trazodone (WAKO) was added, and serotonin (5HT) was added thereto 5 to 10 min after the addition of the trazodone. The initial viable cell count was measured three hr after the addition of serotonin (5HT). The viable cell count was again measured three days after the cell seeding, and the survival rate was calculated based on the initial viable cell count. The cell count measurement was carried out under a phase-contrast microscope using marks previously applied on the backside of the Greiner 4-well dish as a reference. Only cells, which had a large cell body (not less than about 15 μmϕ) and were phase bright, were measured.

2. Experimental Results

The results are shown in FIG. 5. It was found that the antidepressant trazodone had a strong 5HT2A receptor antagonist activity (Giannangeli M., et al., J. Med. Chem., 42, 336-345, 1999). Accordingly, trazodone was evaluated in the rat motor neuron primary pure culture system prepared in Example 1. As a result, trazodone inhibited 5HT excitotoxicity at a low concentration of not more than 1 nM. The evaluation of the survival activity using the culture system was analyzed by using analysis of variance and Dunnett test/Bonferoni test.

Example 5

Evaluation of Compound 1 having Serotonin Receptor (Serotonin 1A Receptor and Serotonin 2A Receptor) Antagonist Activity in Rat Motor Neuron Primary Pure Culture System 1. Experimental Conditions and Experimental Method Rat motor neuron primary pure culture was carried out in the same manner as in Example 1 to prepare rat motor neuron cells. Based on the results of cell measurement, the rat motor neuron cells were diluted with the culture solution to 1.1 to 1.2×10⁴ cells/mL. Greiner 4-well dishes previously coated with poly-L-ornithine/laminin were seeded with the cell suspension at 90 µL/well with a 1 mL Pipetman. One hr after the start of culture, compound 1 was added, and serotonin (5HT) was added thereto 5 to 10 min after the addition of the compound 1. The initial viable cell count was measured three hr after the addition of serotonin (5HT). The viable cell count was again measured three days after the cell seeding, and the survival rate was calculated based on the initial viable cell count. The cell count measurement was carried out under a phase-contrast microscope using marks previously applied on the backside of the Greiner 4-well dish as a reference. Only cells, which had a large cell body (not less than about 15 µmϕ) and were phase bright, were measured.

2. Experimental Results

The results are shown in FIG. 6. The results of the study on the inhibition of 5HT excitotoxicity by compound 1 show that compound 1 inhibits 5HT excitotoxicity at a concentration of not less than 0.1 nM. The evaluation of the survival activity using the culture system was analyzed by using analysis of variance and Dunnett test/Bonferoni test.

Reference Examples

Binding Test on Serotonin 1A and Serotonin 2 Receptors (Animal)
SD rats (six to eight week olds) were used.
(Preparation of Receptor Source)
Rats were slaughtered with a guillotine to extirpate the cerebrum. The hippocampus and cortex were separated from the cerebrum. The hippocampus was used in a serotonin 1A receptor binding test, and the cerebral cortex was used in a serotonin 2 receptor binding test. The hippocampus was homogenized in a 0.32 M sucrose solution in an amount fifty times larger than the wet weight of the hippocampus with a teflon (trademark) glass homogenizer, and the cerebral cortex was homogenized in a 0.32 M sucrose solution in an amount ten times larger than the wet weight of the cerebral cortex with a teflon (trademark) glass homogenizer. Each mixture was centrifuged at 1,000×g for 10 min. The resultant supernatant was further centrifuged at 20,000×g for 20 min. For the hippocampus, the sediment thus obtained was resuspended in 50 mM Tris hydrochloride (pH 7.4) in an amount fifty times larger than the initial wet weight of the hippocampus, and, for the cerebral cortex, the sediment thus obtained was resuspended in 50 mM Tris hydrochloride (pH 7.4) in an amount ten times larger than the initial wet weight of the cerebral cortex. Each suspension was incubated at room temperature for 30 min and was then centrifuged at 20,000×g for 20 min. The sediment thus obtained was further suspended and centrifuged twice in the same manner as described above. For the hippocampus, the sediment thus obtained was suspended in 50 mM Tris hydrochloride (pH 7.4) in an amount one hundred times larger than the initial wet weight of the hippocampus to give a receptor fraction, and, for the cerebral cortex, the sediment thus obtained was suspended in 50 mM Tris hydrochloride (pH 7.4) in an amount twenty times larger than the initial wet weight of the cerebral cortex to give a receptor fraction. The receptor fractions were stored at −80° C. until use.

Binding Test on [³H] 8-hydroxy-dipropylaminotetralin

A test compound and 0.5 nM [³H]8-hydroxy-dipropylaminotetralin were mixed with the receptor fraction of the hippocampus, and the mixture was incubated at room temperature for 30 min. The incubated mixture was filtered through a glass filter with a cell harvester. After washing the glass filter with 50 mM Tris hydrochloride (pH 7.4), the radioactivity bound to the receptor was measured with a liquid scintillation counter. The binding detected in the presence of 10 µM serotonin binoxalate was regarded as nonspecific binding.

Binding Test on [³H] Ketanserin

A test compound and 0.3 nM [³H] ketanserin were mixed with the receptor fraction of the cerebral cortex, and the mixture was incubated at 37° C. for 15 min. The incubated mixture was filtered through a glass filter with a cell harvester. After washing the glass filter with 50 mM Tris hydrochloride (pH 7.4), the radioactivity bound to the receptor was measured with a liquid scintillation counter. The binding detected in the presence of 1 µM methysergide was regarded as nonspecific binding.

$IC_{50}$ value was calculated by the probit method, and Ki value was determined by the following equation.

$$Ki=IC_{50}/(1+c/Kd)$$

wherein c represents the concentration of the radioactive ligand; and Kd represents the dissociation constant of the radioactive ligand with respect to the receptor determined by the Scatchard's analysis.

The results of evaluation of the binding ability of compounds 1 to 6 to serotonin 1A and serotonin 2 receptors by the above testing method are shown in the table below.

|  | 5HT1a (nM) | 5HT2 (nM) |
| --- | --- | --- |
| Compound 1 | 0.65 | 38.15 |
| Compound 2 | 1.58 | 0.75 |
| Compound 3 | 1.18 | 0.96 |
| Compound 4 | 3.70 | 0.05 |
| Compound 5 | 3.86 | 8.00 |
| Compound 6 | 0.70 | 6.40 |

The results of evaluation of the binding ability of compounds 7 and 8 to serotonin 1A and serotonin 2 receptors by the above testing method are shown in the table below.

|  | 5HT1a (nM) | 5HT2 (nM) |
| --- | --- | --- |
| Compound 7 | 18.8 | 3.9 |
| Compound 8 | 54.87 | 1.35 |

Confirmation Test for Serotonin 2 Receptor Antagonist Activity (Mouse Head Twitch Behavior Test)
The serotonin 2 receptor antagonist activity of test compounds was determined by a mouse head twitch behavior test. Tryptamine is a serotonin 2 receptor agonist and is known to induce mouse head twitch behavior through a serotonin 2 receptor. Accordingly, the serotonin 2 receptor antagonist activity of the test compounds can be evaluated based on the head twitch behavior by tryptamine. Tryptamine was administered intravenously to mice at 30 mg/kg, and the number of times of appearance of the head twitch within one min after the start of administration counted. The test compounds (compounds 1 and 4) were administered 15 min before the intravenous administration of tryptamine.

Figure 7:
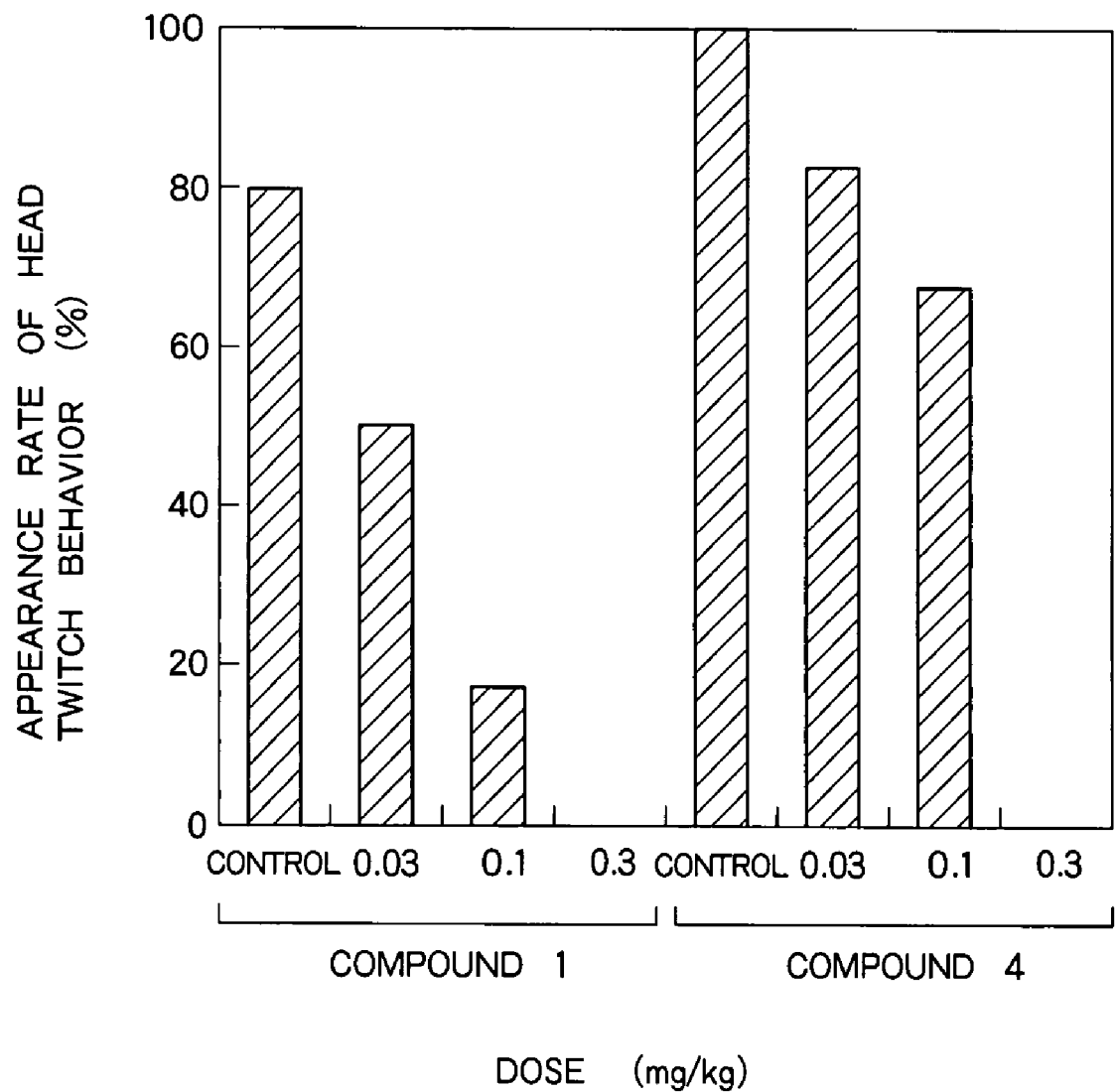
FIG. 7 is a diagram showing the results of a mouse head twitch behavior test.

The results of evaluation of compounds 1 and 4 for serotonin 2 receptor antagonist activity by the above testing method are shown in FIG. 7.

Test on Affinity for Serotonin 1A Receptor

The affinity of test compounds for the 5-HT1A receptor was determined by an experiment for inhibition of a test compound against the binding of [$^3$H]-4-(2'-Methoxy)phenyl-1-[2'-(N-2"-pyridinyl)-p-fluorobenzamido]ethyl-piperazine (MPPF), selectively bound to the 5-HT1A receptor, to a swine hippocampus membrane fraction. The 5-HT1A receptor, which is a G protein binding receptor, is brought to a G protein bound state upon the addition of $MgCl_2$, and is brought to a G protein nonbound state upon the addition of guanylylimidodiphosphate (Gpp(NH)p). It is generally known that a G protein receptor agonist has stronger affinity for the G protein bound receptor depending upon the level of the intrinsic activity. Accordingly, the affinity of a test compound for the receptor in a G protein nonbound state and the affinity of the test compound for the receptor in a G protein bound state were determined and compared with each other to estimate the level of the intrinsic activity of the test compound.

Theoretically, when the value (L/H) obtained by dividing the affinity for the receptor that is in a low affinity state ($IC_{50}$ value) by the affinity for the receptor that is in a high affinity state ($IC_{50}$ value) is not more than 1, the intrinsic activity thereof is zero. The greater this value, the higher the intrinsic activity. Actually, it was regarded that, when the test compound had an L/H value of not more than 1, the test compound had no intrinsic activity while, when the test compound had an L/H value of not less than 2, the test compound had intrinsic activity.

Swine hippocampus was homogenized in an ice-cooled 50 mM Tris hydrochloride buffer (pH 7.4; hereinafter referred to as buffer A). The suspension was centrifuged at 40,000×g for 15 min. The resultant sediment was suspended in buffer A, and the suspension was then centrifuged at 40,000×g for 15 min. The same procedure was further repeated twice or three times. The finally obtained sediment was suspended in buffer A in an amount of about ten times larger than the wet weight of the swine hippocampus to prepare a membrane fraction which was then stored at −80° C. until use.

A mixture (0.5 mL) for incubation, containing an appropriate amount of the membrane fraction, a test compound in a desired concentration, $MgCl_2$ (final concentration: 10 mM) or Gpp(NH)p (final concentration: 1 mM), [$^3$H]MPPF (final concentration: 0.5 nM), dimethyl sulfoxide (final concentration: 1% (v/v)), and 50 mM Tris hydrochloride buffer (pH 7.4), was provided. Upon the addition of the membrane fraction, a reaction started, and the mixture was incubated at 37° C. for 30 min. After the incubation, the incubated mixture was suction filtered through a glass filter with a cell harvester. After washing the glass filter with ice-cooled buffer A, the radioactivity bound to the receptor was measured with a liquid scintillation counter. The binding detected in the presence of 10 μM WAY-100,635. was regarded as nonspecific binding.

Data on affinity in terms of $IC_{50}$ value determined from an inhibition curve are shown in the table below.

|  | Low affinity (nM) | High affinity (nM) | L/H ratio |
| --- | --- | --- | --- |
| Compound 9 | 0.16 | 0.2 | 0.8 |
| Compound 10 | 0.1 | 0.13 | 0.8 |
| Compound 11 | 0.15 | 0.17 | 0.9 |
| Compound 12 | 0.34 | 0.46 | 0.7 |
| Compound 13 | 0.35 | 0.27 | 1.3 |
| Compound 14 | 0.26 | 0.16 | 1.6 |
| Compound 15 | 0.15 | 0.16 | 0.9 |

Observation

[$^3$H]8-hydroxy-dipropylaminotetralin is known to be used for the measurement of binding of test compounds to serotonin 1A receptors (European Journal of Pharmacology, 90, p. 151-153, 1983.). Further, [$^3$H]ketanserin is known to be used for the measurement of binding of test compounds to serotonin 2A receptors (Brian Dean and Wendy Hayes, Schizophrenia Research, 21, p. 133-139, 1996.). Furthermore, the test on mouse head twitch behavior with tryptamine is known to be used for the measurement of the serotonin 2 receptor antagonist activity of test compounds (Yamada J., et al., European Journal of Pharmacology, 140, p. 323-330, 1987; and Yamada J., et al., Neuropharmacology, 26, p. 49-53, 1987.).

It was confirmed that compounds 1 and 4 had excellent serotonin 2A receptor antagonist activity. It was suggested that compounds 2, 3, 5 and 6 have serotonin 2A receptor antagonist activity. Further, it was suggested that compounds 1 to 6 have serotonin 1A receptor antagonist activity.

Likewise, it was suggested that compounds 7 and 8 have serotonin receptor (serotonin 1A receptor and serotonin 2A receptor) antagonist activity.

Further, it was confirmed that compounds 9 to 15 had excellent serotonin 1A receptor antagonist activity (see pamphlet of International Publication 2005/108389).

What is claimed is:

1. A method for treating a motor neuron disease, comprising the step of administering a therapeutically effective amount of a compound having serotonin receptor antagonist activity or its pharmacologically acceptable salt or their solvate optionally together with a pharmaceutically acceptable carrier to a mammal for which the treatment of said disease is indicated.

2. The method according to claim 1, characterized in that said compound having serotonin receptor antagonist activity is a compound having 5HT1A receptor antagonist activity and/or 5HT2A receptor antagonist activity.

3. The method according to claim 2, wherein said compound having 5HT2A receptor antagonist activity is selected from the group consisting of sarpogrelate, trazodone, nortriptyne, amitriptine, imipramine, paroxetine, fluvoxamine, milnacipran, mirtazapine, mianserin, MDL-11939, MDL100907, olanzapine, risperidone, perospirone, quetiapine, clocapramine, carpipramine, mosapramine, chlorpromazine, and levomepromazine.

4. The method according to claim 1, wherein said compound having serotonin receptor antagonist activity is represented by formula (I):

[Chemical formula 1]

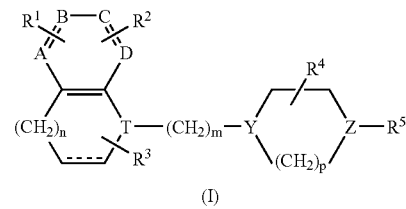

(I)

wherein

A, B, C, and D, which may be the same or different, represent methine or a nitrogen atom, provided that at least two of them represent methine, ---represents a single or double bond, T represents methine or a nitrogen atom, Y and Z, which may be the same or different, represent methine, a nitrogen atom, a group represented by the following formula

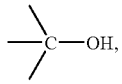

[Chemical formula 2]

or a group represented by the following formula

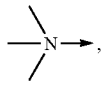

[Chemical formula 3]

provided that at least one of them represent a nitrogen atom, $R^1$ and $R^2$, which may be the same or different, represent a hydrogen atom, a halogen atom, hydroxyl, $C_{1-6}$ alkylsulfonylamino $C_{1-6}$ alkyl, halogenated $C_{1-6}$ alkylsulfonylamino $C_{1-6}$ alkyl, 2-pyrrolidinon-1-yl, 1-hydroxy-1-(methoxypyridyl)methyl, methoxypyridylcarbonyl, 1,3-propanesultam-2-yl, hydroxypiperidylcarbonyl $C_{1-6}$ alkyl, hydroxy $C_{1-6}$ alkylamido $C_{1-6}$ alkyl, halogenated $C_{1-6}$ alkylamido $C_{1-6}$ alkyl, dihalogenated $C_{1-6}$ alkylamido $C_{1-6}$ alkyl, heteroarylamido $C_{1-6}$ alkyl, hydroxy $C_{1-6}$ alkylamido $C_{1-6}$ alkyl, optionally substituted amino, nitro, $C_{1-6}$ alkyl, $C_{1-6}$ alkoxy, $C_{1-6}$ acyl, $C_{1-6}$ alkoxy $C_{1-6}$ alkoxy, cyano, $C_{1-6}$ alkylsulfonyl, $C_{1-6}$ alkylsulfonylamido, hydroxy $C_{1-6}$ alkyl, hydroxy $C_{1-6}$ alkoxy, $C_{1-6}$ alkoxycarbonylamino, $C_{1-6}$ alkylsulfonylamino, N—$C_{1-6}$ alkyl $C_{1-6}$ alkylsulfonylamino, $C_{1-6}$ acylamino, optionally substituted amino $C_{1-6}$ alkyl, optionally N-substituted $C_{1-6}$ alkyl $C_{1-6}$ acylamino $C_{1-6}$ alkyl, optionally substituted aryl, optionally substituted arylsulfonylamino, $C_{1-6}$ alkylsulfonyloxy, hydroxyiminomethyl, (2-pyrrolidon-1-yl)methyl, (2-piperidon-1-yl)methyl, optionally substituted heteroaryl, optionally substituted aralkyl, optionally substituted heteroaryl $C_{1-6}$ alkyl, $C_{3-6}$ cycloalkylcarbonylamino $C_{1-6}$ alkyl, optionally substituted ureido, optionally substituted ureido $C_{1-6}$ alkyl, succinimide, (succinimido-1-yl) $C_{1-6}$ alkyl, amide, optionally substituted carbamoyl, optionally substituted carbamoyl $C_{1-6}$ alkyl, optionally substituted thiocarbamoyl $C_{1-6}$ alkyl, $C_{1-6}$ alkylaminothiocarbonylamino $C_{1-6}$ alkyl, formyl, arylcarbonyl, heteroarylcarbonyl, halogenated $C_{1-6}$ alkyl, (2-imidazolidinon-1-yl)methyl, (2,4-imidazolidinedion-3-yl)methyl, (2-oxazolidon-3-yl)methyl, (glutarimido-1-yl)methyl, optionally substituted heteroarylhydroxy $C_{1-6}$ alkyl, cyano $C_{1-6}$ alkyl, 1-hydroxy $C_{3-6}$ cycloalkyl, (2,4-thiazolidinedion-3-yl)methyl, optionally substituted 4-piperidylmethyl, aryl $C_{1-6}$ acyl, heteroaryl $C_{1-6}$ acyl, pyrrolidinylcarbonyl $C_{1-6}$ alkyl, optionally substituted aminosulfonyl $C_{1-6}$ alkyl, carboxy $C_{1-6}$ alkyl, or $C_{1-6}$ alkylamido $C_{1-6}$ alkyl, or alternatively $R^1$ and $R^2$ together may form an optionally substituted alicyclic ring, an optionally substituted heterocyclic ring, or alkylenedioxy, provided that these rings are optionally substituted, $R^3$ represents a hydrogen atom, a halogen atom, $C_{1-6}$ alkyl, hydroxyl, hydroxy $C_{1-6}$ alkyl, $C_{1-6}$ alkoxy, formyl, optionally substituted aralkyloxy, hydroxy $C_{1-6}$ alkoxy, optionally substituted sulfamoyl, or optionally N-substituted sulfamoyl $C_{1-6}$ alkyl, $R^4$ represents a hydrogen atom, $C_{1-6}$ alkyl, hydroxy $C_{1-6}$ alkyl, $C_{1-6}$ alkoxy $C_{1-6}$ alkyl, aryloxy $C_{1-6}$ alkyl in which the aryl group is optionally substituted, or aralkyloxy $C_{1-6}$ alkyl in which the aryl group is optionally substituted, $R^5$ represents $C_{1-6}$ alkyl, $C_{1-6}$ acyl, $C_{1-6}$ alkoxycarbonyl, arylcarbonyl, aryl $C_{1-6}$ acyl, or a group represented by the following formula

 [Chemical formula 4]

wherein both Q1 and Q2 represent a single bond, or any one of Q1 and Q2 is a single bond while the other represents an oxygen atom, carbonyl, a group represented by formula —NHCO—, a group represented by formula —NHSO$_2$—, or a group represented by formula >CH—$R^7$ wherein $R^7$ represents hydroxyl, $C_{1-6}$ alkyl, or a halogen atom, s is zero (0), or an integer of 1 to 6, $R^6$ represents a group selected from optionally substituted aryl, optionally substituted heteroaryl, or optionally substituted condensed heterocyclic group, n is zero (0) or an integer of 1 to 3, m is zero (0) or an integer of 1 to 6, and p is an integer of 1 to 3.

5. The method according to claim 4, wherein all of A, B, C, and D represent methine.

6. The method according to claim 4, wherein ⁓ represents a double bond.

7. The method according to claim 4, wherein T represents a nitrogen atom.

8. The method according to claim 4, wherein Y represents methine and Z represents a nitrogen atom.

9. The method according to claim 4, wherein, when one of $R^1$ and $R^2$ represents a hydrogen atom, the other substituent represents $C_{1-6}$ alkylsulfonylamino $C_{1-6}$ alkyl, $C_{1-6}$ alkoxy, optionally substituted carbamoyl, optionally substituted carbamoyl $C_{1-6}$ alkyl, $C_{1-6}$ alkylamido $C_{1-6}$ alkyl, or $C_{1-6}$ alkylaminothiocarbonylamino $C_{1-6}$ alkyl.

10. The method according to claim 9, wherein, when one of $R^1$ and $R^2$ represents a hydrogen atom, the other substituent represents methylsulfonylaminomethyl, methoxy, carbamoyl optionally substituted by methyl, carbamoylmethyl optionally substituted by methyl, methylamidomethyl, or methylaminothiocarbonylaminomethyl.

11. The method according to claim 4, wherein $R^3$ represents a hydrogen atom.

12. The method according to claim 4, wherein $R^4$ represents a hydrogen atom.

13. The method according to claim 4, wherein $R^5$ is represented by the following formula:

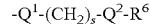 [Chemical formula 5]

wherein both $Q^1$ and $Q^2$ represent a single bond; s is 2; and $R^6$ represents optionally substituted aryl, optionally substituted heteroaryl, or an optionally substituted condensed heterocyclic group.

14. The method according to claim 13, wherein $R^6$ represents optionally substituted phenyl, optionally substituted pyridyl, optionally substituted quinolyl, optionally substituted chromanyl, optionally substituted benzoxazolyl, optionally substituted benzisoxazolyl, or benzo[1,4]dioxanyl.

15. The method according to claim 4, wherein n is zero (0).

16. The method according to claim 4, wherein m is zero (0).

17. The method according to claim 4, wherein p is 2.

18. The method according to claim 4, wherein all of A, B, C, and D represent methine; represents a double bond; T represents a nitrogen atom; Y represents methine; Z represents a nitrogen atom; when one of $R^1$ and $R^2$ represents a hydrogen atom, the other substituent represents $C_{1-6}$ alkylsulfonylamino $C_{1-6}$ alkyl, $C_{1-6}$ alkoxy, optionally substituted carbamoyl, optionally substituted carbamoyl $C_{1-6}$ alkyl, $C_{1-6}$ alkylamido $C_{1-6}$ alkyl, or $C_{1-6}$ alkylaminothiocarbonylamino $C_{1-6}$ alkyl; $R^3$ represents a hydrogen atom; $R^4$ represents a hydrogen atom; $R^5$ is represented by the following formula:

-Q$^1$-(CH$_2$)$_s$-Q$^2$-R$^6$      [Chemical formula 6] 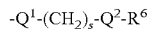

wherein both $Q^1$ and $Q^2$ represent a single bond, s is 2, $R^6$ represents optionally substituted aryl, optionally substituted heteroaryl, or optionally substituted condensed heterocyclic group; m is zero (0); n is zero (0); and p is 2.

19. The method according to claim 4, wherein all of A, B, C, and D represent methine; represents a double bond; T represents a nitrogen atom; Y represents methine; Z represents a nitrogen atom; when one of $R^1$ and $R^2$ represents a hydrogen atom, the other substituent represents methylsulfonylaminomethyl, methoxy, carbamoyl optionally substituted by methyl, carbamoylmethyl optionally substituted by methyl, methylamidomethyl, or methylaminothiocarbonylamino methyl; $R^3$ represents a hydrogen atom; $R^4$ represents a hydrogen atom; $R^5$ is represented by the following formula:

-Q$^1$-(CH$_2$)$_s$-Q$^2$-R$^6$      [Chemical formula 7] 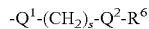

wherein both $Q^1$ and $Q^2$ represent a single bond, s is 2, $R^6$ represents optionally substituted phenyl, optionally substituted pyridyl, optionally substituted quinolyl, optionally substituted chromanyl, optionally substituted benzoxazolyl, optionally substituted benzisoxazolyl, or benzo[1,4]dioxanyl; m is zero (0); n is zero (0); and p is 2.

20. The method according to claim 1, wherein the compound having serotonin receptor antagonist activity is represented by formula (II):

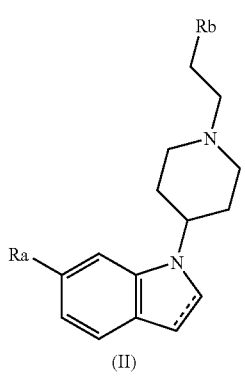

[Chemical formula 8]

(II)

wherein

Ra represents a hydrogen atom, a halogen atom, hydroxyl, $C_{1-6}$ alkylsulfonylamino $C_{1-6}$ alkyl, halogenated $C_{1-6}$ alkylsulfonylamino $C_{1-6}$ alkyl, 2-pyrrolidinon-1-yl, 1-hydroxy-1-(methoxypyridyl)methyl, methoxypyridylcarbonyl, 1,3-propanesultam-2-yl, hydroxypiperidylcarbonyl $C_{1-6}$ alkyl, hydroxy $C_{1-6}$ alkylamido $C_{1-6}$ alkyl, halogenated $C_{1-6}$ alkylamido $C_{1-6}$ alkyl, dihalogenated $C_{1-6}$ alkylamido $C_{1-6}$ alkyl, heteroarylamido $C_{1-6}$ alkyl, hydroxy $C_{1-6}$ alkylamido $C_{1-6}$ alkyl, optionally substituted amino, nitro, $C_{1-6}$ alkyl, $C_{1-6}$ alkoxy, $C_{1-6}$ acyl, $C_{1-6}$ alkoxy $C_{1-6}$ alkoxy, cyano, $C_{1-6}$ alkylsulfonyl, $C_{1-6}$ sulfonylamido, hydroxy $C_{1-6}$ alkyl, hydroxy $C_{1-6}$ alkoxy, $C_{1-6}$ alkoxycarbonylamino, $C_{1-6}$ alkylsulfonylamino, N—$C_{1-6}$ alkyl $C_{1-6}$ alkylsulfonylamino, $C_{1-6}$ acylamino, optionally substituted amino $C_{1-6}$ alkyl, optionally N-substituted $C_{1-6}$ alkyl $C_{1-6}$ acylamino $C_{1-6}$ alkyl, optionally substituted aryl, optionally substituted arylsulfonylamino, $C_{1-6}$ alkylsulfonyloxy, hydroxyiminomethyl, (2-pyrrolidon-1-yl)methyl, (2-piperidon-1-yl)methyl, optionally substituted heteroaryl, optionally substituted aralkyl, optionally substituted heteroaryl $C_{1-6}$ alkyl, $C_{3-6}$ cycloalkylcarbonylamino $C_{1-6}$ alkyl, optionally substituted ureido, optionally substituted ureido $C_{1-6}$ alkyl, succinimide, (succinimido-1-yl) $C_{1-6}$ alkyl, amide, optionally substituted carbamoyl, optionally substituted carbamoyl $C_{1-6}$ alkyl, optionally substituted thiocarbamoyl $C_{1-6}$ alkyl, $C_{1-6}$ alkylaminothiocarbonylamino $C_{1-6}$ alkyl, formyl, aryl $C_{1-6}$ acyl, arylcarbonyl, heteroarylcarbonyl, halogenated $C_{1-6}$ alkyl, (2-imidazolidinon-1-yl)methyl, (2,4-imidazolidinedion-3-yl)methyl, (2-oxazolidon-3-yl)methyl, (glutarimido-1-yl)methyl, optionally substituted heteroarylhydroxyalkyl, cyano $C_{1-6}$ alkyl, 1-hydroxy $C_{3-6}$ cycloalkyl, (2,4-thiazolidinedion-3-yl)methyl, optionally substituted 4-piperidylmethyl, heteroaryl $C_{1-6}$ acyl, pyrrolidinylcarbonyl $C_{1-6}$ alkyl, optionally substituted aminosulfonyl $C_{1-6}$ alkyl, carboxy $C_{1-6}$ alkyl, or $C_{1-6}$ alkylamido $C_{1-6}$ alkyl, Rb represents optionally substituted aryl, optionally substituted heteroaryl, or an optionally substituted condensed heterocyclic group, and represents a single bond or a double bond.

21. The method according to claim 20, wherein Ra represents $C_{1-6}$ alkylsulfonylamino $C_{1-6}$ alkyl, $C_{1-6}$ alkoxy, optionally substituted carbamoyl, optionally substituted carbamoyl $C_{1-6}$ alkyl, $C_{1-6}$ alkylamido $C_{1-6}$ alkyl, or $C_{1-6}$ alkylaminothiocarbonylamino $C_{1-6}$ alkyl.

22. The method according to claim 21, wherein Ra represents methylsulfonylaminomethyl, methoxy, carbamoyl optionally substituted by methyl, carbamoylmethyl optionally substituted by methyl, methylamidomethyl, or methylaminothiocarbonylamino methyl.

23. The method according to claim 20, wherein Rb represents optionally substituted phenyl, optionally substituted pyridyl, optionally substituted quinolyl, optionally substituted chromanyl, optionally substituted benzoxazolyl, optionally substituted benzisoxazolyl, or benzo[1,4]dioxanyl.

24. The method according to claim 20, wherein represents a double bond.

25. The method according to claim 20, wherein Ra represents $C_{1-6}$ alkylsulfonylamino $C_{1-6}$ alkyl, $C_{1-6}$ alkoxy, optionally substituted carbamoyl, optionally substituted carbamoyl $C_{1-6}$ alkyl, $C_{1-6}$ alkylamido $C_{1-6}$ alkyl, or $C_{1-6}$ alkylaminothiocarbonylamino $C_{1-6}$ alkyl; Rb represents optionally substituted phenyl, optionally substituted pyridyl, optionally substituted quinolyl, optionally substituted chromanyl, optionally substituted benzoxazolyl, optionally substituted benzisoxazolyl, or benzo[1,4]dioxanyl; and represents a double bond.

26. The method according to claim 20, wherein Ra represents methylsulfonylaminomethyl, methoxy, carbamoyl optionally substituted by methyl, carbamoylmethyl optionally substituted by methyl, methylamidomethyl, or methylaminothiocarbonylaminomethyl; Rb represents optionally substituted phenyl, optionally substituted pyridyl, optionally substituted quinolyl, optionally substituted chromanyl, optionally substituted benzoxazolyl, optionally substituted benzisoxazolyl, or benzo[1,4]dioxanyl; and ═══ represents a double bond.

27. The method according to claim 1, wherein the compound having serotonin receptor antagonist activity is represented by formula (III):

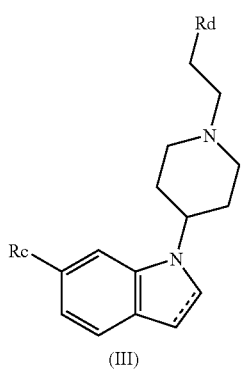

[Chemical formula 9]

(III)

wherein
Rc represents $C_{1-6}$ alkylsulfonylamino $C_{1-6}$ alkyl, $C_{1-6}$ alkoxy, optionally substituted carbamoyl, optionally substituted carbamoyl $C_{1-6}$ alkyl, $C_{1-6}$ alkylamido $C_{1-6}$ alkyl, or $C_{1-6}$ alkylaminothiocarbonylamino $C_{1-6}$ alkyl,
Rd represents phenyl optionally having one to four substituents selected from the following substituent group A1, or substituted phenyl in which two adjacent substituents, together with two carbon atoms to which they are attached, form a five- to seven-membered ring non-aromatic hydrocarbocyclic group, a five- to seven-membered ring non-aromatic heterocyclic group, a six-membered ring aromatic hydrocarbocyclic group, or a five- or six-membered ring aromatic heterocyclic group, which may be substituted by one to four substituents selected from the following substituent group B1,
wherein said substituent group A1 consists of (1) a hydrogen atom, (2) a halogen atom, (3) cyano, (4) hydroxyl, (5) nitro, (6) carboxyl, (7) $C_{3-8}$ cycloalky, (8) $C_{2-6}$ alkenyl, (9) $C_{2-6}$ alkynyl, (10) $C_{1-6}$ alkylthio, (11) $C_{1-6}$ alkoxycarbonyl, (12) $C_{1-6}$ alkylsulfonyl, (13) $C_{1-6}$ alkyl optionally substituted by one to three substituents selected from the group consisting of a halogen atom, hydroxyl and $C_{1-6}$ alkoxy, (14) $C_{1-6}$ alkoxy optionally substituted by one to three halogen atoms, (15) amino optionally substituted by a substituent selected from the group consisting of $C_{1-6}$ alky, formyl, $C_{1-6}$ alkanoyl and $C_{1-6}$ alkylsulfonyl, and (16) carbamoyl optionally substituted by one or two $C_{1-6}$ alkyls, and
said substituent group B1 consists of (1) a hydrogen atom, (2) a halogen atom, (3) cyano, (4) hydroxyl, (5) nitro, (6) oxo, (7) carboxyl, (8) $C_{3-8}$ cycloalkyl, (9) $C_{2-6}$ alkenyl, (10) $C_{2-6}$ alkynyl, (11) $C_{1-6}$ alkylthio, (12) $C_{1-6}$ alkoxycarbonyl, (13) $C_{1-6}$ alkylsulfonyl, (14) $C_{1-6}$ alkyl optionally substituted by a halogen atom, hydroxyl and $C_{1-6}$ alkoxy, (15) $C_{1-6}$ alkoxy optionally substituted by one to three halogen atoms, (16) amino optionally substituted by a substituent selected from the group consisting of $C_{1-6}$ alkyl, formyl, $C_{1-6}$ alkanoyl and $C_{1-6}$ alkylsulfonyl, (17) carbamoyl optionally substituted by one or two $C_{1-6}$ alkyls, (18) $C_{1-6}$ alkoxyimino, (19) $C_{5-6}$ cycloalkyl formed by two $C_{1-3}$ alkyls attached to the same carbon atom, and (20) tetrahydropyranyl formed by two $C_{1-3}$ alkyls attached to the same carbon atom, together with an oxygen atom and the carbon atom, and ═══ represents a single bond or a double bond.

28. The method according to claim 27, wherein Rc represents methylsulfonylaminomethyl, methoxy, carbamoyl optionally substituted by methyl, carbomoylmethyl optionally substituted by methyl, methylamidomethyl, or methylaminothiocarbonylamino methyl.

29. The method according to claim 27, wherein Rd represents phenyl substituted by a halogen atom.

30. The method according to claim 27, wherein Rd represents substituted phenyl in which adjacent substituents, which together with two carbon atoms to which they are attached, form a group represented by the following group:

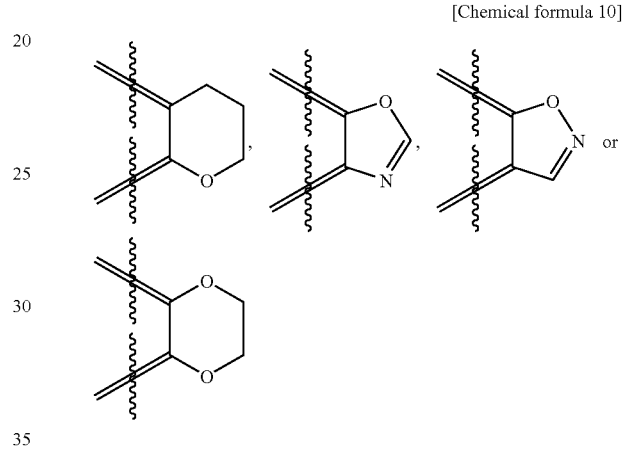

[Chemical formula 10]

wherein hydrogen atoms on each cyclic group are optionally substituted by one to four substituents selected from the following substituent group B1,
wherein said substituent group B1 consists of (1) a hydrogen atom, (2) a halogen atom, (3) cyano, (4) hydroxyl, (5) nitro, (6) oxo, (7) carboxyl, (8) $C_{3-8}$ cycloalkyl, (9) $C_{2-6}$ alkenyl, (10) $C_{2-6}$ alkynyl, (11) $C_{1-6}$ alkylthio, (12) $C_{1-6}$ alkoxycarbonyl, (13) $C_{1-6}$ alkylsulfonyl, (14) $C_{1-6}$ alkyl optionally substituted by a halogen atom, hydroxyl and $C_{1-6}$ alkoxy, (15) $C_{1-6}$ alkoxy optionally substituted by one to three halogen atoms, (16) amino optionally substituted by a substituent selected from the group consisting of $C_{1-6}$ alkyl, formyl, $C_{1-6}$ alkanoyl and $C_{1-6}$ alkylsulfonyl, (17) carbamoyl optionally substituted by one or two $C_{1-6}$ alkyls, (18) $C_{1-6}$ alkoxyimino, (19) $C_{5-6}$ cycloalkyl formed by two $C_{1-3}$ alkyls attached to the same carbon atom, and (20) tetrahydropyranyl formed by two $C_{1-3}$ alkyls attached to the same carbon atom, together with an oxygen atom and the carbon atom.

31. The method according to claim 27, wherein ═══ represents a double bond.

32. The method according to claim 27, wherein Rc represents methylsulfonylaminomethyl, methoxy, carbamoyl optionally substituted by methyl, carbamoylmethyl optionally substituted by methyl, methylamidomethyl, or methylaminothiocarbonylamino methyl; Rd represents phenyl substituted by a halogen atom, or substituted phenyl in which adjacent substituents, which together with two carbon atoms to which they are attached, from a group represented by the following group:

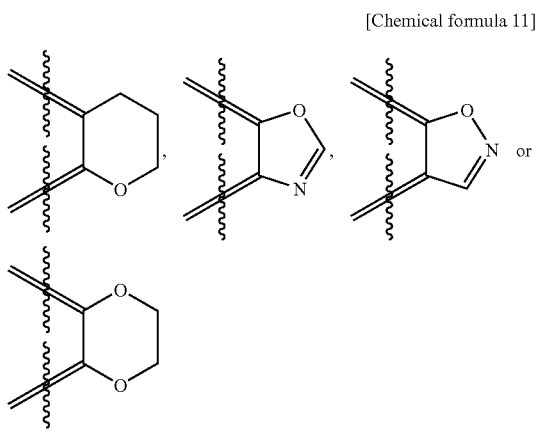

wherein hydrogen atoms on each cyclic group are optionally substituted by one to four substituents selected from the following substituent group B1, wherein said substituent group B1 consists of (1) a hydrogen atom, (2) a halogen atom, (3) cyano, (4) hydroxyl, (5) nitro, (6) oxo, (7) carboxyl, (8) $C_{3-8}$ cycloalkyl, (9) $C_{2-6}$ alkenyl, (10) $C_{2-6}$ alkynyl, (11) $C_{1-6}$ alkylthio, (12) $C_{1-6}$ alkoxycarbonyl, (13) $C_{1-6}$ alkylsulfonyl, (14) $C_{1-6}$ alkyl optionally substituted by a halogen atom, hydroxyl and $C_{1-6}$ alkoxy, (15) $C_{1-6}$ alkoxy optionally substituted by one to three halogen atoms, (16) amino optionally substituted by a substituent selected from the group consisting of $C_{1-6}$ alkyl, formyl, $C_{1-6}$ alkanoyl and $C_{1-6}$ alkysulfonyl, (17) carbamoyl optionally substituted by one or two $C_{1-6}$ alkyls, (18) $C_{1-6}$ alkoxyimino, (19) $C_{5-6}$ cycloalkyl formed by two $C_{1-3}$ alkyls attached to the same carbon atom, and (20) tetrahydropyranyl formed by two $C_{1-3}$ alkyls attached to the same carbon atom, together with an oxygen atom and the carbon atom; and ═ represents a double bond.

33. The method according to claim 1, wherein said compound having serotonin receptor antagonist activity is represented by formula (IV):

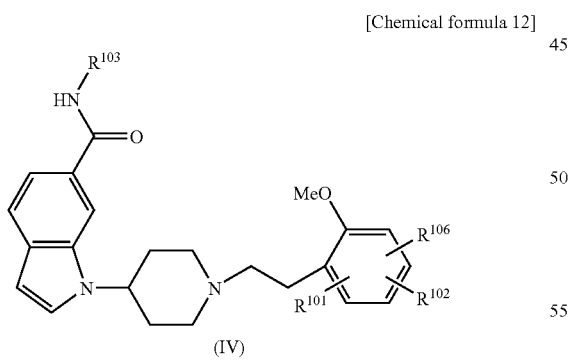

wherein $R^{101}$ and $R^{102}$ are mutually adjacent substituents which, together with two carbon atoms to which they are attached, form
(1) a five- to seven-membered ring non-aromatic hydrocarbocyclic group,
(2) a five- to seven-membered ring non-aromatic heterocyclic group,
(3) a six-membered ring aromatic hydrocarbocyclic group, or
(4) a five- or six-membered ring aromatic heterocyclic group, which may be substituted by 1 to 4 substituents selected from the following substituent group B1, $R^{103}$ represents a hydrogen atom or methyl, $R^{106}$ represents a substituent selected from the following substituent group A1, said substituent group A1 consists of (1) a hydrogen atom, (2) a halogen atom, (3) cyano, (4) hydroxyl, (5) nitro, (6) carboxyl, (7) $C_{3-8}$ cycloalkyl, (8) $C_{2-6}$ alkenyl, (9) $C_{2-6}$ alkynyl, (10) $C_{1-6}$ alkylthio, (11) $C_{1-6}$ alkoxycarbonyl, (12) $C_{1-6}$ alkylsulfonyl, (13) $C_{1-6}$ alkyl optionally substituted by one to three substituents selected from the group consisting of a halogen atom, hydroxyl and $C_{1-6}$ alkoxy, (14) $C_{1-6}$ alkoxy optionally substituted by one to three halogen atoms, (15) amino optionally substituted by a substituent selected from the group consisting of $C_{1-6}$ alkyl, formyl, $C_{1-6}$ alkanoyl and $C_{1-6}$ alkylsulfonyl, and (16) carbamoyl optionally substituted by one or two $C_{1-6}$ alkyls, and said substituent group B1 consists of (1) a hydrogen atom, (2) a halogen atom, (3) cyano, (4) hydroxyl, (5) nitro, (6) oxo, (7) carboxyl, (8) $C_{3-8}$ cycloalkyl, (9) $C_{2-6}$ alkenyl, (10) $C_{2-6}$ alkynyl, (11) $C_{1-6}$ alkylthio, (12) $C_{1-6}$ alkoxycarbonyl, (13) $C_{1-6}$ alkylsulfonyl, (14) $C_{1-6}$ alkyl optionally substituted by a halogen atom, hydroxyl and $C_{1-6}$ alkoxy, (15) $C_{1-6}$ alkoxy optionally substituted by one to three halogen atoms, (16) amino optionally substituted by a substituent selected from the group consisting of $C_{1-6}$ alkyl, formyl, $C_{1-6}$ alkanoyl and $C_{1-6}$ alkylsulfonyl, (17) carbamoyl optionally substituted by one or two $C_{1-6}$ alkyls, (18) $C_{1-6}$ alkoxyimino, (19) $C_{5-6}$ cycloalkyl formed by two $C_{1-3}$ alkyls attached to the same carbon atom, and (20) tetrahydropyranyl formed by two $C_{1-3}$ alkyls attached to the same carbon atom, together with an oxygen atom and the carbon atom.

34. The method according to claim 33, wherein $R^{101}$ and $R^{102}$ are mutually adjacent substituents which, together with two carbon atoms to which they are attached, form a group represented by the following group:

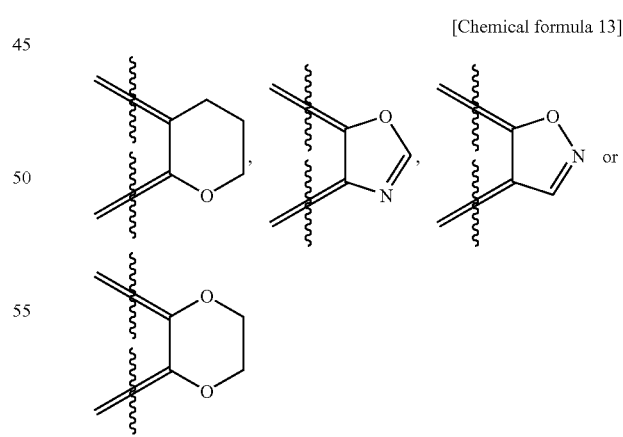

wherein hydrogen atoms on each cyclic group are optionally substituted by one to four substituents selected from the following substituent group B1, wherein said substituent group B1 consists of (1) a hydrogen atom, (2) a halogen atom, (3) cyano, (4) hydroxyl, (5) nitro, (6) oxo, (7) carboxyl, (8) $C_{3-8}$ cycloalkyl, (9) $C_{2-6}$ alkenyl,

(10) $C_{2-6}$ alkynyl, (11) $C_{1-6}$ alkylthio, (12) $C_{1-6}$ alkoxycarbonyl, (13) $C_{1-6}$ alkylsulfonyl, (14) $C_{1-6}$ alkyl optionally substituted by a halogen atom, hydroxyl and $C_{1-6}$ alkoxy, (15) $C_{1-6}$ alkoxy optionally substituted by one to three halogen atoms, (16) amino optionally substituted by a substituent selected from the group consisting of $C_{1-6}$ alkyl, formyl, $C_{1-6}$ alkanoyl and $C_{1-6}$ alkylsulfonyl, (17) carbamoyl optionally substituted by one or two $C_{1-6}$ alkyls, (18) $C_{1-6}$ alkoxyimino, (19) $C_{5-6}$ cycloalkyl formed by two $C_{1-3}$ alkyls attached to the same carbon atom, and (20) tetrahydropyranyl formed by two $C_{1-3}$ alkyls attached to the same carbon atom, together with an oxygen atom and the carbon atom.

35. The method according to claim 33, wherein $R^{106}$ is unsubstituted.

36. The method according to claim 33, wherein $R^{101}$ and $R^{102}$ are mutually adjacent substituents which, together with two carbon atoms to which they are attached, form a group represented by the following group:

[Chemical formula 14]

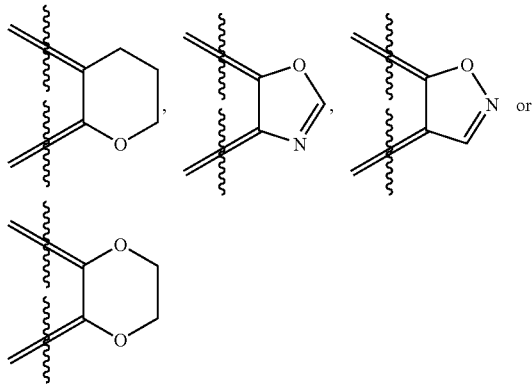

wherein hydrogen atoms on each cyclic group are optionally substituted by one to four substituents selected from the following substituent group B1, wherein said substituent group B1 consists of (1) a hydrogen atom, (2) a halogen atom, (3) cyano, (4) hydroxyl, (5) nitro, (6) oxo, (7) carboxyl, (8) $C_{3-8}$ cycloalkyl, (9) $C_{2-6}$ alkenyl, (10) $C_{2-6}$ alkynyl, (11) $C_{1-6}$ alkylthio, (12) $C_{1-6}$ alkoxycarbonyl, (13) $C_{1-6}$ alkylsulfonyl, (14) $C_{1-6}$ alkyl optionally substituted by a halogen atom, hydroxyl and $C_{1-6}$ alkoxy, (15) $C_{1-6}$ alkoxy optionally substituted by one to three halogen atoms, (16) amino optionally substituted by a substituent selected from the group consisting of $C_{1-6}$ alkyl, formyl, $C_{1-6}$ alkanoyl and $C_{1-6}$ alkylsulfonyl, (17) carbamoyl optionally substituted by one or two $C_{1-6}$ alkyls, (18) $C_{1-6}$ alkoxyimino, (19) $C_{5-6}$ cycloalkyl formed by two $C_{1-3}$ alkyls attached to the same carbon atom, and (20) tetrahydropyranyl formed by two $C_{1-3}$ alkyls attached to the same carbon atom, together with and oxygen atom and the carbon atom; and $R^{106}$ is unsubstituted.

37. The method according to claim 1, wherein the compound having serotonin receptor antagonist activity is selected from the following group of compounds:
(1) N-methyl-{1-[1-(2-fluorophenethyl)piperidin-4-yl]-1H-indol-6-yl}acetamide,
(2) N-{1-[1-(2-fluorophenethyl)piperidin-4-yl]-1H-indol-6-yl}methylacetamide,
(3) 1-{1-[1-(2-fluorophenethyl)piperidin-4-yl]-1H-indol-6-yl}methyl-3-methylthiourea,
(4) N-{1-[1-(2-fluorophenethyl)piperidin-4-yl]-1H-indolin-6-yl}methylacetamide,
(5) N-{1-[1-(4-fluorophenethyl)piperidin-4-yl]1H-indolin-6-yl}methyl-methanesulfonamide,
(6) 1-[1-(4-fluorophenethyl)piperidin-4-yl]-6-methoxyindoline,
(7) 2-{4-[1-(4-ethylpiperazin-1-yl)isoquinolin-3-yl]phenoxy}ethanol,
(8) 1-{4-[4-(4-ethylpiperazin-1-yl)thieno[3,2-c]pyridin-6-yl]phenoxy}-2-methylpropan-2-ol,
(9) 1-{1-[2-(7-methoxy-2,2-dimethyl-4-oxochroman-8-yl) ethyl]piperidin-4-yl}-N-methyl-1H-indole-6-carboxamide,
(10) 1-{1-[2-(7-methoxy-2,2-dimethyl-4-oxochroman-8-yl) ethyl]piperidin-4-yl}-1H-indole-6-carboxamide,
(11) 1-{1-[2-(6-methoxy-2-methylbenzoxazol-5-yl) ethyl]piperidin-4-yl}-1H-indole-6-carboxamide,
(12) 1-{1-[2-(6-methoxy-2-methylbenzoxazol-7-yl) ethyl]piperidin-4-yl}-1H-indole-6-carboxamide,
(13) 1-{1-[2-(6-methoxy-3-methylbenzo[d]isoxazol-5-yl) ethyl]piperidin-4-yl}-1H-indole-6-carboxamide,
(14) 1-{1-[2-(6-methoxy-3-methylbenzo[d]isoxazol-7-yl) ethyl]piperidin-4-yl}-1H-indole-6-carboxamide, and
(15) 1-{1-[2-(7-methoxy-2,3-dihydrobenzo[1,4]dioxin-6-yl) ethyl]piperidin-4-yl}-1H-indole-6-carboxamide.

38. The method according to claim 1, wherein the motor neuron disease is selected from the group consisting of diffuse atrophic paralysis, pseudobulbar palsy, familiar amyotrophic lateral sclerosis, bulbar palsy, amyotrophic lateral sclerosis, juvenile unilateral upper-limb muscular atrophy, progressive bulbar palsy, progressive muscular dystrophy, and spinal progressive muscular atrophy.

39. A method for treating a motor neuron disease, comprising the step of selectively inhibiting a serotonin receptor in a mammal for which the treatment of said disease is indicated.

* * * * *